US012588815B2

(12) United States Patent
Huang et al.

(10) Patent No.: US 12,588,815 B2
(45) Date of Patent: Mar. 31, 2026

(54) PHYSIOLOGICAL SIGNAL MONITORING DEVICE

(71) Applicant: BIONIME CORPORATION, Taichung City (TW)

(72) Inventors: Chun-Mu Huang, Taichung City (TW); Chieh-Hsing Chen, Taichung City (TW); Chen-Hao Lee, Taichung City (TW)

(73) Assignee: Bionime Corporation, Taichung City (TW)

( * ) Notice: Subject to any disclaimer, the term of this patent is extended or adjusted under 35 U.S.C. 154(b) by 74 days.

(21) Appl. No.: 16/983,174

(22) Filed: Aug. 3, 2020

(65) Prior Publication Data

US 2021/0030273 A1 Feb. 4, 2021

Related U.S. Application Data

(60) Provisional application No. 62/882,140, filed on Aug. 2, 2019.

(30) Foreign Application Priority Data

Jan. 10, 2020 (TW) ................................. 109100959

(51) Int. Cl.
A61B 5/00 (2006.01)
A61B 5/145 (2006.01)

(52) U.S. Cl.
CPC ........ *A61B 5/0002* (2013.01); *A61B 5/14503* (2013.01); *A61B 5/14546* (2013.01); *A61B 5/1451* (2013.01); *A61B 5/14532* (2013.01)

(58) Field of Classification Search
CPC .............. A61B 5/0002; A61B 5/14503; A61B 5/14546; A61B 5/1451; A61B 5/14532
See application file for complete search history.

(56) References Cited

U.S. PATENT DOCUMENTS 8,792,953 B2 7/2014 Brister et al.
8,792,955 B2 7/2014 Brister et al.
(Continued)

FOREIGN PATENT DOCUMENTS

CN 102613978 A 8/2012
CN 204351841 U 5/2015
(Continued)

OTHER PUBLICATIONS

A Search Report, which was issued to European counterpart application No. 20189225.4 by the EPO on Nov. 24. 2020.
(Continued)

*Primary Examiner* — Abid A Mustansir
(74) *Attorney, Agent, or Firm* — Perkins Coie LLP; Viola Kung; Gautam Thatte

(57) ABSTRACT

A physiological signal monitoring device includes a base, a biosensor mounted to the base, a transmitter, and a sealing unit. The base is adapted to be mounted to a skin surface of a host. The biosensor includes a mounting seat and a sensing member that is mounted to the mounting seat. The sensing member is adapted to be partially inserted underneath the skin surface of the host for measuring an analyte of the host and to send a corresponding physiological signal. The transmitter is for receiving and transmitting the physiological signal, and has a bottom portion. The transmitter covers the base while the bottom portion faces the base. The sensing member is coupled to the transmitter. The sealing unit is used to seal paths through which a liquid possibly penetrates into an interior of the physiological signal monitoring device so as to avoid damage of the device.

14 Claims, 22 Drawing Sheets

(56) References Cited

U.S. PATENT DOCUMENTS

| | | | |
|---|---|---|---|
| 8,886,272 | B2 | 11/2014 | Brister et al. |
| 10,031,124 | B2 | 7/2018 | Galasso |
| 10,278,732 | B2 | 5/2019 | Schoonmaker et al. |
| 10,327,638 | B2 | 6/2019 | Brister et al. |
| 11,207,006 | B2 * | 12/2021 | Love .................. A61B 5/14532 |
| 2006/0195029 | A1 | 8/2006 | Shults et al. |
| 2013/0150691 | A1 * | 6/2013 | Pace ................ A61B 5/150748 |
| | | | 600/347 |
| 2013/0267813 | A1 | 10/2013 | Pryor et al. |
| 2015/0374270 | A1 | 12/2015 | Shults et al. |
| 2016/0058470 | A1 | 3/2016 | Peterson et al. |
| 2016/0058474 | A1 | 3/2016 | Peterson et al. |
| 2016/0287150 | A1 | 10/2016 | Yu |
| 2017/0188912 | A1 | 7/2017 | Halac et al. |
| 2017/0290533 | A1 | 10/2017 | Antonio et al. |
| 2017/0290535 | A1 | 10/2017 | Rao et al. |
| 2017/0290546 | A1 | 10/2017 | Antonio et al. |
| 2018/0055432 | A1 | 3/2018 | Chen |
| 2018/0271414 | A1 | 9/2018 | Deck et al. |
| 2019/0076071 | A1 | 3/2019 | Brister et al. |
| 2019/0083017 | A1 * | 3/2019 | Walter ............... A61B 5/14532 |
| 2019/0183396 | A1 | 6/2019 | Shults et al. |
| 2019/0320956 | A1 | 10/2019 | Pryor et al. |
| 2020/0178899 | A1 | 6/2020 | Chae et al. |
| 2020/0330007 | A1 * | 10/2020 | Garai ..................... H01L 23/66 |

FOREIGN PATENT DOCUMENTS

| | | |
|---|---|---|
| CN | 105816184 A | 8/2016 |
| CN | 106137214 A | 11/2016 |
| CN | 107014877 A | 8/2017 |
| CN | 109998560 A | 7/2019 |
| EP | 3202324 A1 | 8/2017 |
| WO | 2009051802 A2 | 4/2009 |
| WO | 2011011643 A1 | 1/2011 |
| WO | 2013090215 A2 | 6/2013 |
| WO | 2013152090 A2 | 10/2013 |
| WO | 2016036924 A2 | 3/2016 |
| WO | 2017116915 A1 | 7/2017 |
| WO | 2018222012 A1 | 12/2018 |

OTHER PUBLICATIONS

An International Search Report, which was issued to PCT application No. PCT/IB2020/057261 by the WIPO on Nov. 27, 2020.

* cited by examiner

11

313

4

42

31

315

114

21(213)

PHYSIOLOGICAL SIGNAL MONITORING DEVICE

CROSS-REFERENCE TO RELATED APPLICATION

This application claims priority of U.S. Provisional Patent Application No. 62/882,140, filed on Aug. 2, 2019, and Taiwanese Patent Application No. 109100959, filed on Jan. 10, 2020.

FIELD

The disclosure relates to a monitoring device, and more particularly to a physiological signal monitoring device.

BACKGROUND

Continuous glucose monitoring (CGM) is a popular method for tracking changes in blood glucose levels by taking glucose measurements of an individual at regular intervals. In order to utilize a CGM system, the individual wears a form of compact, miniature sensing device, which at least includes a biosensor for sensing physiological signal corresponding to the glucose level of a host, and a transmitter for receiving and sending the abovementioned physiological signal.

As a conventional CGM system, it is meant to be worn by the host over a prolonged period of time, and thus incorporating leakage prevention to the design of the device becomes just as important, so as to prevent contaminated liquid from damaging internal component of the sensing device and from infecting wounds that were previously formed due to the insertion of the device. However, as the biosensors and the transmitters available in the market are usually individually packaged and are required to be assembled by an user before use, the sensing device is more easily exposed to leakage if the user has not securely coupled the sensing device together before use.

In addition, as the user has to use an insertion tool to insert the biosensor of the conventional CGM system sensing device beneath a skin surface of the host, blood bursting out of the wound during the insertion process may not be a comfortable sight for the user or the host. In addition, if the transmitter is coupled to the biosensor right after the insertion process, the blood flowing out of the wound may also damage the internal components of the device as it flow through a location where the biosensor and the transmitter are coupled to one another.

SUMMARY

Therefore, an object of the disclosure is to provide a physiological signal monitoring device that can alleviate at least one of the drawbacks of the prior art.

According to one aspect of the disclosure, the physiological signal monitoring device includes a base, a biosensor, a transmitter, and a sealing unit. The base is adapted to be mounted to a skin surface of a host. The biosensor is mounted to the base and includes a mounting seat and a sensing member. The mounting seat has a bottom surface and a top surface, and is formed with a fitting hole that extends through the top and bottom surfaces. The sensing member is carried by the mounting seat, is partially extending through the fitting hole, and is adapted to be partially inserted underneath the skin surface of the host for measuring at least one analyte of the host and to send a corresponding physiological signal. The fitting hole of the mounting seat is adapted for an insertion tool to removably extend therethrough to guide the sensing member to be partially inserted underneath the skin surface of the host. The transmitter is removably mounted to the base, is for receiving and transmitting the physiological signal, and has a bottom portion. The bottom portion faces the base when the transmitter is mounted to the base so as to allow the mounting seat to be disposed between the base and the transmitter and to allow the sensing member to be coupled to the transmitter. The sealing unit includes an urging module that is disposed between the bottom portion of the transmitter and the fitting hole of the mounting seat and sealing the fitting hole for sealing an implantation path.

According to another aspect of the disclosure, the physiological signal monitoring device includes a base, a biosensor, a transmitter, and a sealing unit. The base a bottom plate that is adapted to be mounted to a skin surface of a host, and an inner surrounding wall that protrudes from a top surface of the bottom plate. The inner surrounding wall and the bottom plate cooperatively define a mounting groove therebetween.

The biosensor is mounted to the base and includes a mounting seat and a sensing member. The mounting seat is mounted to the mounting groove of the base. The sensing member is carried by the mounting seat, and is adapted to be partially inserted underneath a skin surface of a host for measuring at least one analyte of the host and to send a corresponding physiological signal. The transmitter is removably mounted to the base, is for receiving and transmitting the physiological signal, and has a bottom portion. The bottom portion faces the base when the transmitter is mounted to the base so as to allow the mounting seat to be disposed between the base and the transmitter and to allow the sensing member to be coupled to the transmitter. The sealing unit includes a third sealing member that is clamped between an inner peripheral surface of the inner surrounding wall of the base and an outer surrounding surface of the mounting seat for sealing a first liquid leakage pathway.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
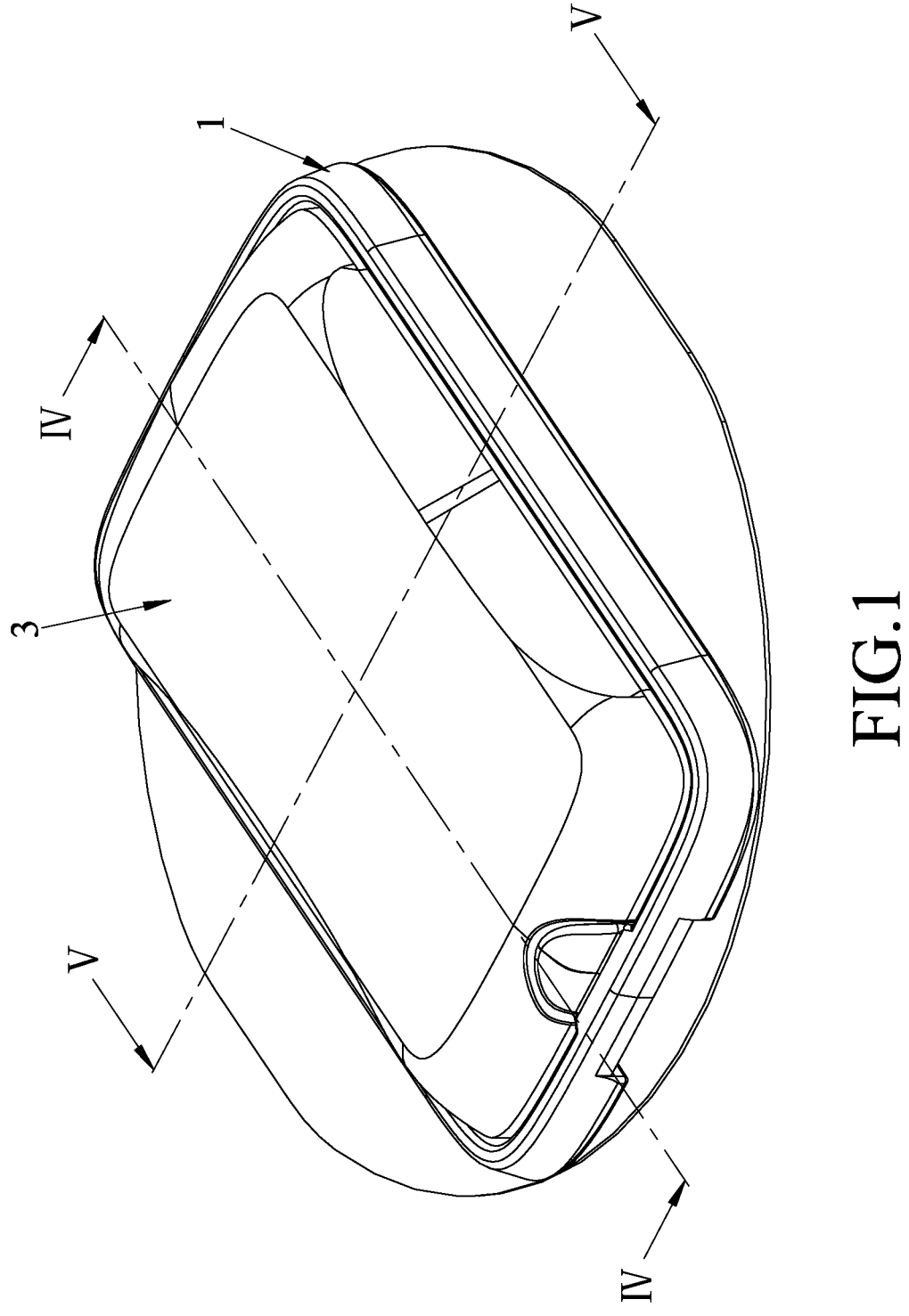
FIG. 1 is a perspective view of a first embodiment of a physiological signal monitoring device according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

In addition, in the description of the disclosure, the terms "up", "down", "top", "bottom" are meant to indicate relative position between the elements of the disclosure, and are not meant to indicate the actual position of each of the elements in actual implementations. Similarly, various axes to be disclosed herein, while defined to be perpendicular to one another in the disclosure, may not be necessarily perpendicular in actual implementation.

Figure 2:
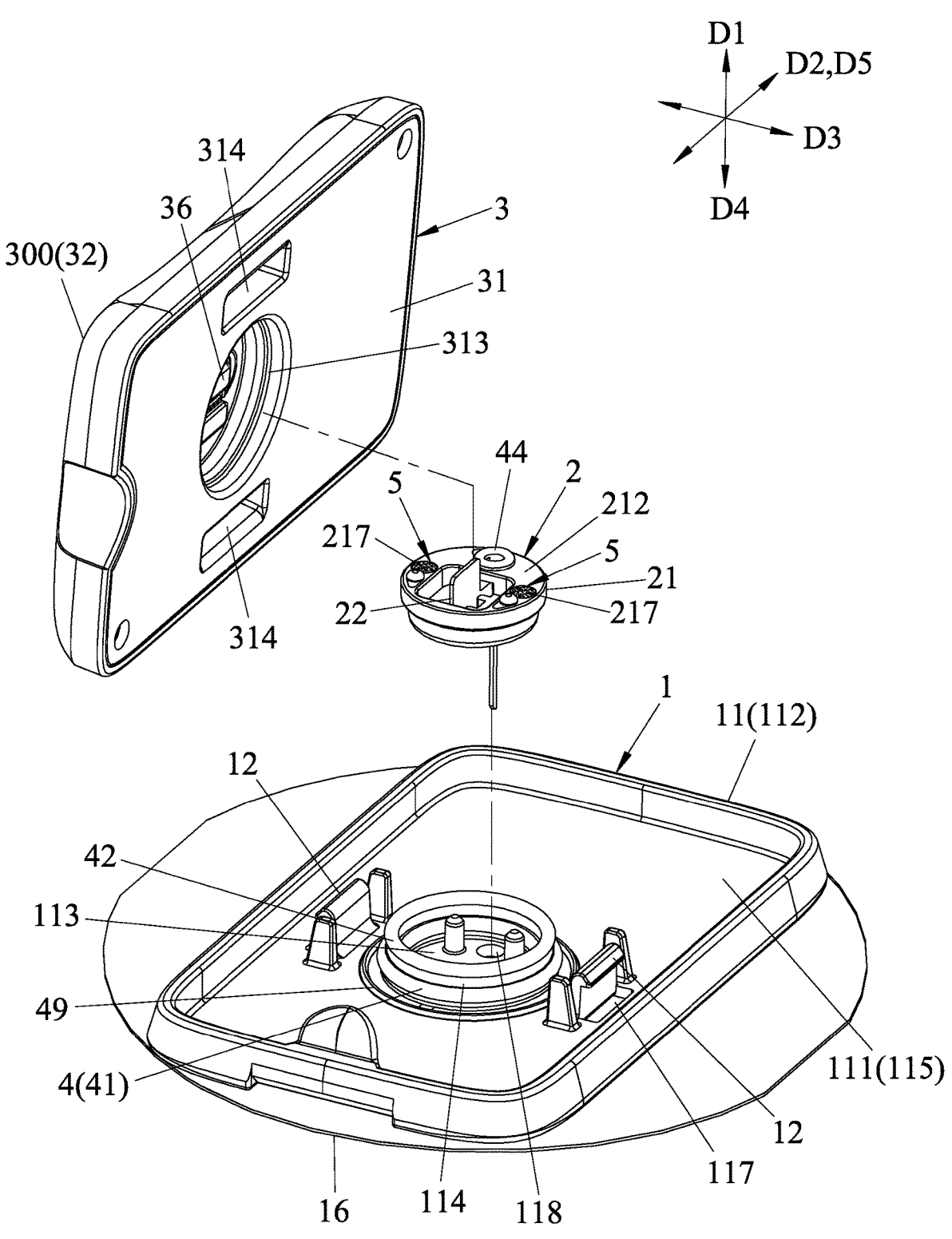
FIG. 2 is an exploded perspective view of the first embodiment.
Figure 3:
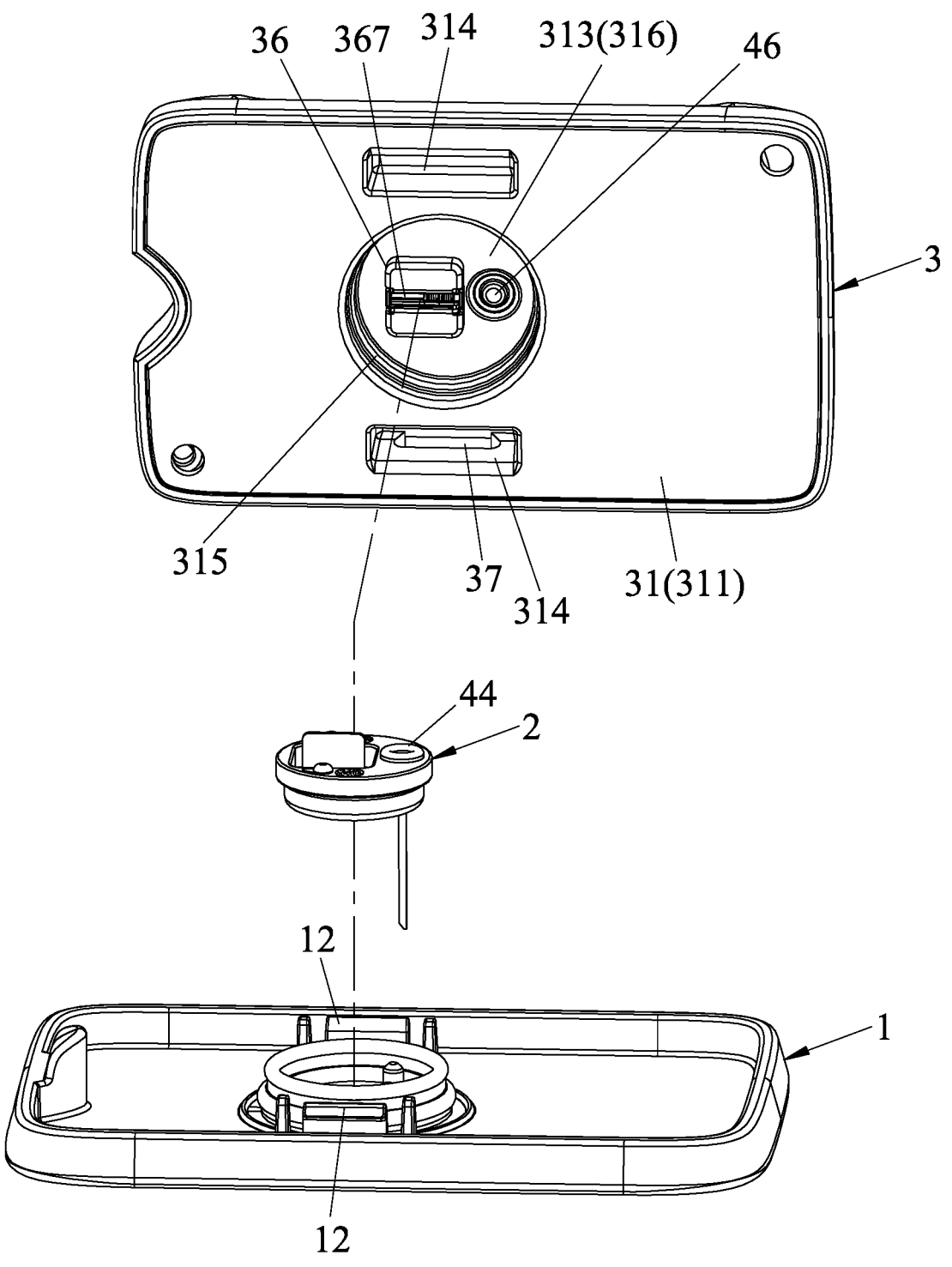
FIG. 3 is another exploded perspective view of the first embodiment.
Figure 8:
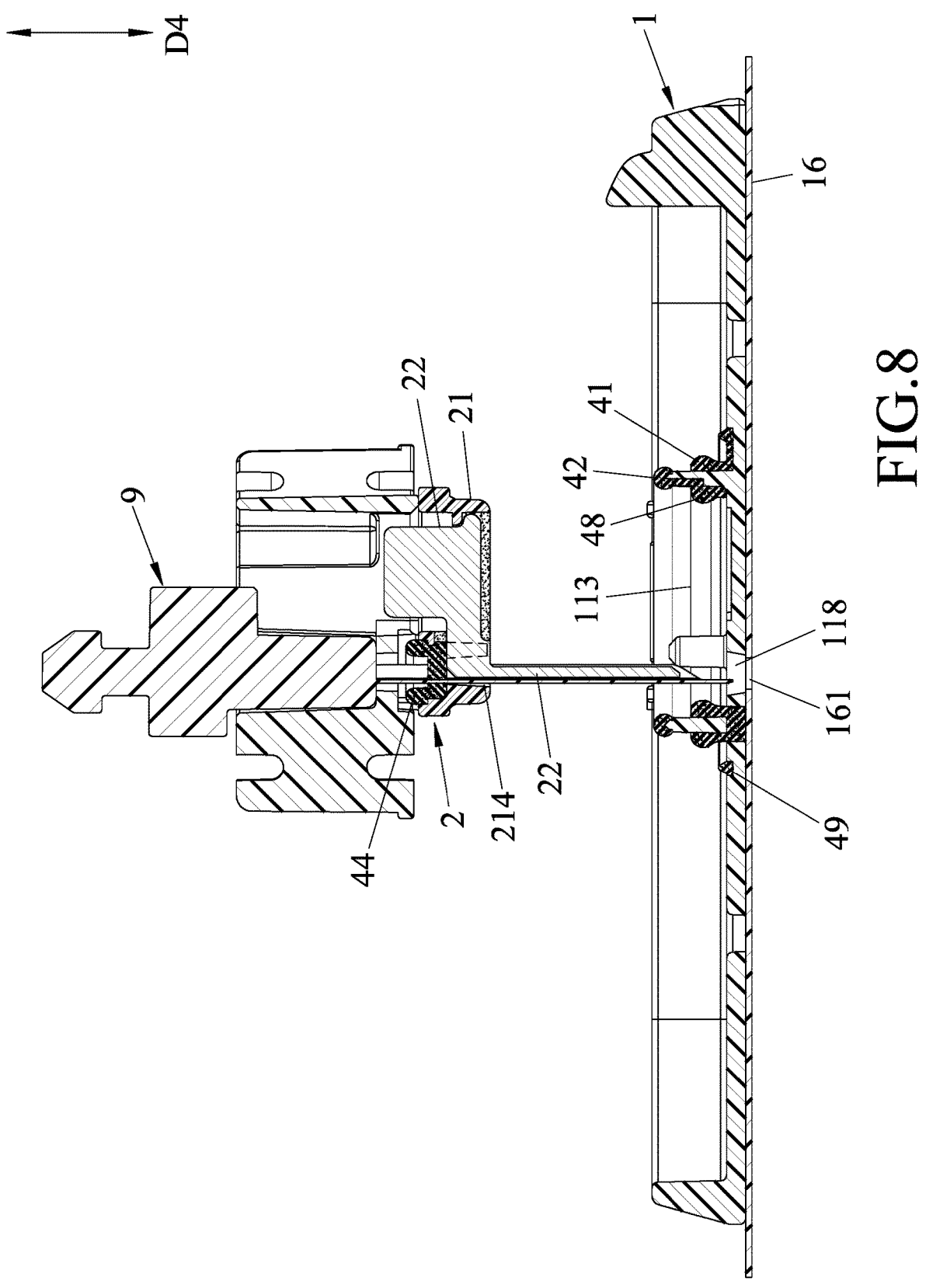
FIGS. 8 and 9 are sectional views of a base and the biosensor of the first embodiment, illustrating the biosensor before and after being coupled to the base via an insertion tool.

Referring to FIGS. 1 and 2, a first embodiment of a physiological signal monitoring device according to the disclosure is adapted to be mounted to a skin surface of a host (not shown) via an insertion tool 9 (see FIG. 8) of an insertion device (not shown) for measuring at least one analyte of the host and for transmitting a corresponding physiological signal corresponding to the analyte. In this embodiment, the physiological signal monitoring device is for measuring the glucose concentration in the interstitial fluid (ISF) of the host, and is meant to be mounted to the skin surface for two weeks, but is not restricted to such. The duration of use of the physiological signal monitoring device may vary depending on the type of material used during the manufacture thereof. The physiological signal monitoring device includes a base 1, a biosensor 2, and a transmitter 3.

Figure 4:
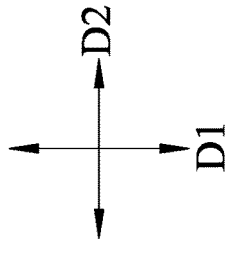
FIG. 4 is a sectional view taken along line IV-IV in FIG. 1.
Figure 5:
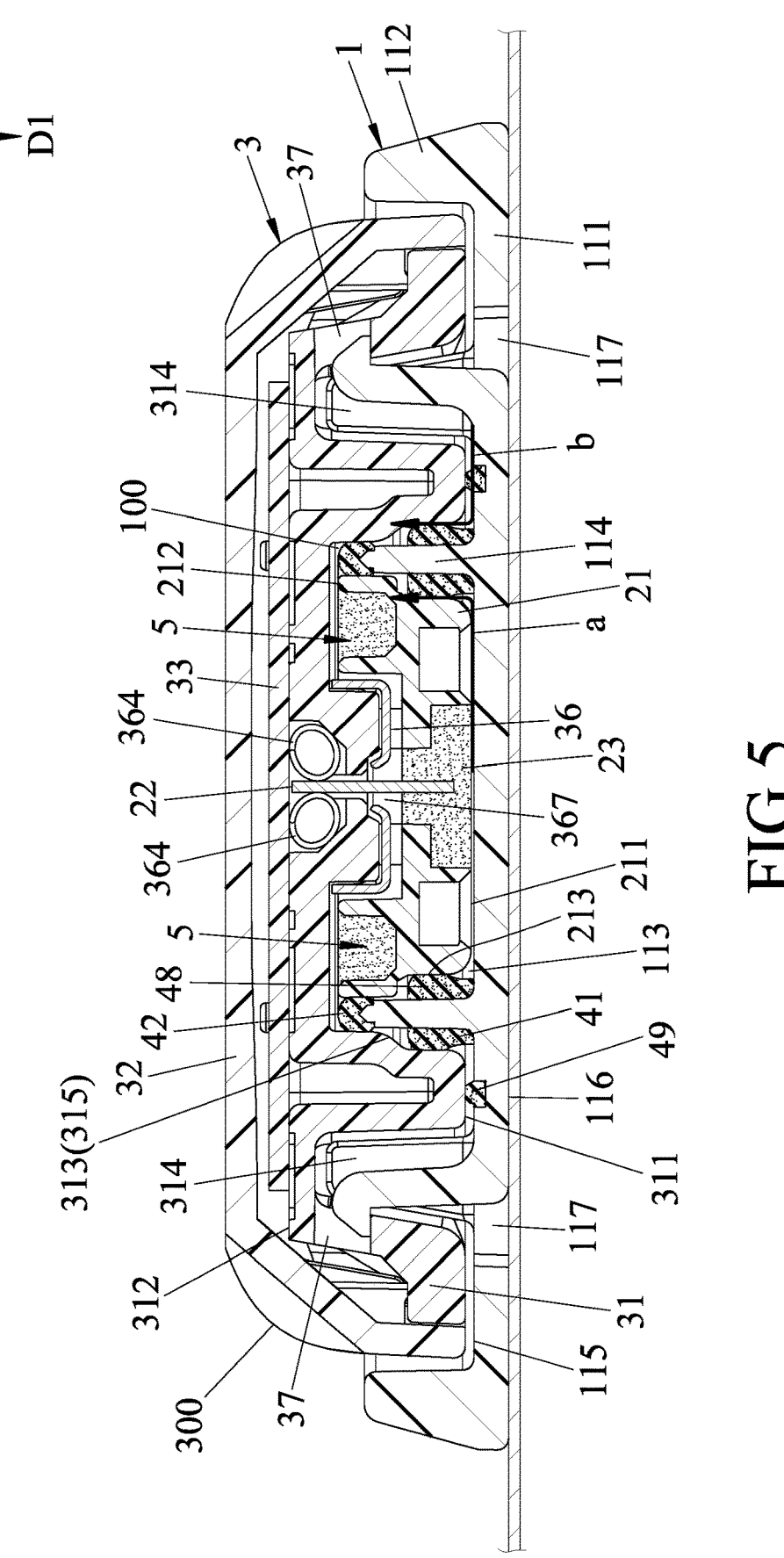
FIG. 5 is a sectional view taken along line V-V in FIG. 1.

Referring to FIGS. 2 and 5, the base 1 includes a base body 11 that has a bottom plate 111 adapted to be mounted to the skin surface of the host and perpendicular to a direction of a first axis (D1), and at least one first coupling structure 12 that is disposed on a top surface 115 of the bottom plate 111. The base body 11 further includes an outer surrounding wall 112 that extends upwardly along the direction of the first axis (D1) from a periphery of the bottom plate 111, an inner surrounding wall 114 that protrudes from the top surface 115 of the bottom plate 111 and that cooperates with the bottom plate 111 to define a mounting groove 113, and at least one opening 117 that extends through the bottom plate 111. The bottom plate 111 has the top surface 115, a bottom surface 116 opposite to the top surface 115 in the direction of the first axis (D1), and a through hole 118 (see FIG. 4) extending through top and bottom surfaces 115, 116 of the bottom plate 111 and communicated to the mounting groove 113. In this embodiment, the number of openings 117 is two, and are spaced apart from the mounting groove 113 in a direction of a third axis (D3), which is perpendicular to the first axis (D1). A second axis (D2), which will be referenced herein, is perpendicular to both the first and third axes (D1, D3). In some embodiments, an angle between every two axes of the first, second and third axes (D1, D2, and D3) is not limited to 90 degrees.

In this embodiment, the base 1 has two of the first coupling structures 12. The first coupling structures 12 protrude from the top surface 115 of the bottom plate 111 of the base body 11, are spaced apart from the mounting groove 113 in the direction of the third axis (D3), and are respectively disposed in proximity to the openings 117.

Referring to FIGS. 2 and 4, the base body 11 is permitted to be attached to the skin surface of the host via an adhesive pad 16. The adhesive pad 16 is mounted to the bottom surface 116 of the bottom plate 111 and has a pad hole 161 that corresponds in position to the through hole 118 of the base body 11, and a waterproof portion 162 that surrounds the pad hole 161. The waterproof portion 162 prevents contaminated liquid, which penetrates into the adhesive pad 16, from moving toward the pad hole 161 and further contaminating wound on the skin surface (caused by piercing of the insertion tool 9) and other components of the physiological signal monitoring device. In this embodiment, the adhesive pad 16 is made of nonwoven fabrics and is applied with adhesives on both sides thereof, one side being attached to the bottom surface 116 of the bottom plate 111 and the other side being attached to the skin surface of the host. In other embodiments, the adhesive pad 16 may be omitted, and the bottom plate 111 is directly adhered to the skin surface of the host. In this embodiment, the waterproof portion 162 is formed by infiltrating gum into the nonwoven fabrics.

The biosensor 2 includes a mounting seat 21 that is mounted to the mounting groove 113 of the base body 11, and a sensing member 22 that is carried and limited by the mounting seat 21, and that is adapted for measuring the at least one analyte of the host and for sending the corresponding physiological signal to the transmitter 3. Referring to FIGS. 2 and 4 to 7, the mounting seat 21 has a bottom surface 211, a top surface 212, and an outer surrounding surface 213 that interconnects the top and bottom surfaces 212, 211, and is formed with a fitting hole 214 that extends through top and bottom surfaces 212, 211 in an inserting direction (D4), and that is adapted for the insertion tool 9 to removably extend therethrough so as to guide the sensing member 22 to be partially inserted underneath the skin surface of the host. The mounting seat 21 defines a mounting space 210 that is disposed between the top and bottom surfaces 212, 211 and that has an open top end. The mounting space 210 and the fitting hole 214 are spaced apart from each other and fluidly communicated with each other in an extending direction (D5). An angle (θ) (see FIG. 7) is defined between the inserting direction (D4) and the extending direction (D5). In this embodiment, the inserting direction (D4) extends in the direction of the first axis (D1), and the extending direction (D5) extends in the direction of the second axis (D2), which is previously disclosed to be perpendicular to both the first and third axes (D1, D3).

However, the extending and inserting directions (D5, D4) may be different in other embodiments.

Figure 6:
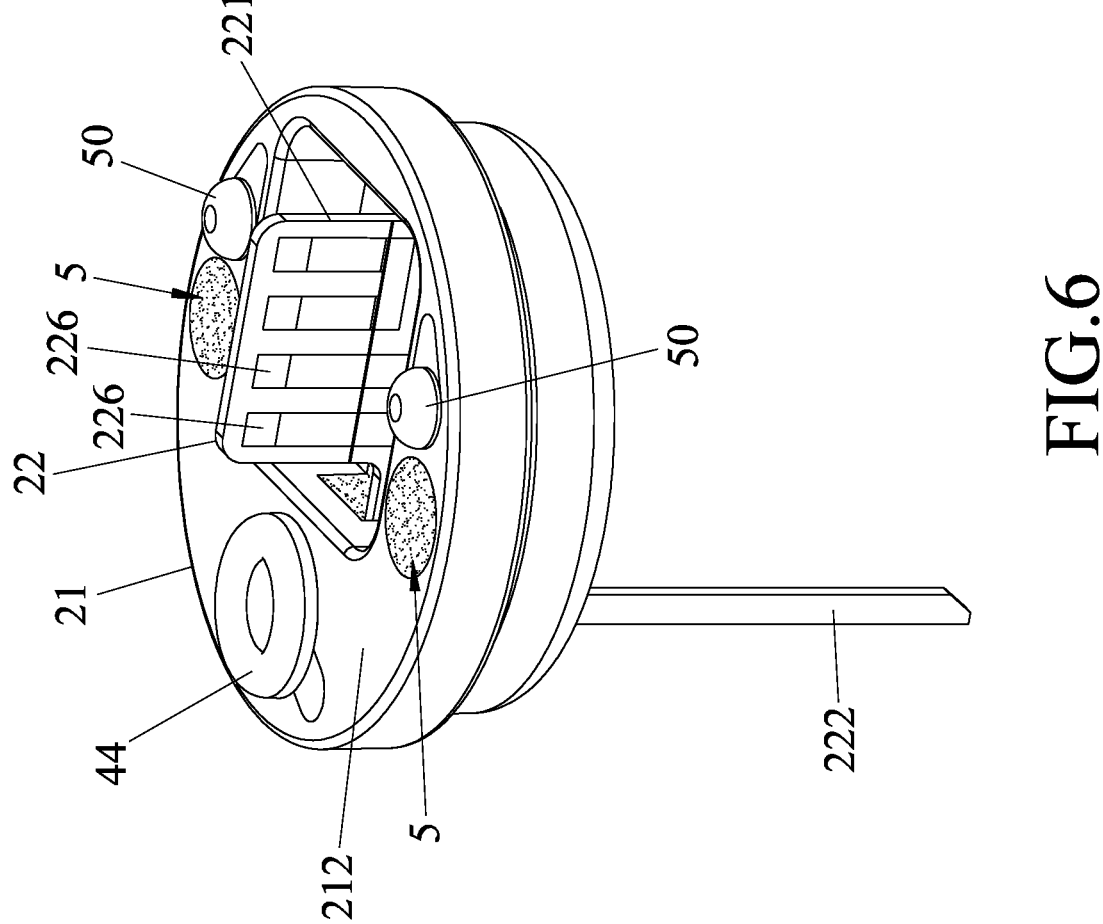
FIG. 6 is a perspective view of a biosensor of the first embodiment.

The sensing member 22 has a sensing section 222, a signal output section 221 and an extended section 223 that interconnects the sensing section 222 and the signal output section 221. The sensing section 222 extends through a bottom portion 214b of the fitting hole 214 and is adapted to be inserted underneath the skin surface of the host for measuring the physiological signal corresponding to the physiological parameter of the at least one analyte of the host. The signal output section 221 is received at the mounting space 210 and electrically connected to the transmitter 3 for transmitting the corresponding physiological signal to the transmitter 3 after receiving information from the sensing section 222 via the extended section 223. The extended section 223 extends from the mounting space 210 to the fitting hole 214. As shown in FIG. 6, the sensing member 22 transmits the physiological signal to the transmitter 3 when at least one output 226 of the signal output section 221 is electrically connected to the transmitter 3. To do so, the sensing member 22 includes a plurality of electrodes that is disposed thereon and that includes the output 226. It should be noted that numbers and types of electrodes mounted on a surface of the sensing member 22 is primarily designed to account for the type of analytes measured, and is not restricted to the one shown in the disclosure. For the sake for clarity, detailed configurations of the output 226 and electric connection terminals of the signal output section 221 of the sensing member 22 are only showcased in FIG. 6.

Figure 7:
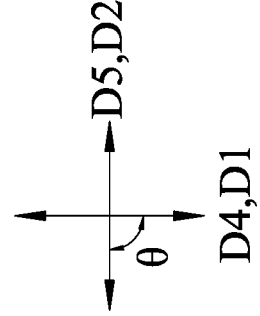
FIG. 7 is a sectional view of the biosensor of the first embodiment.
Figure 7:
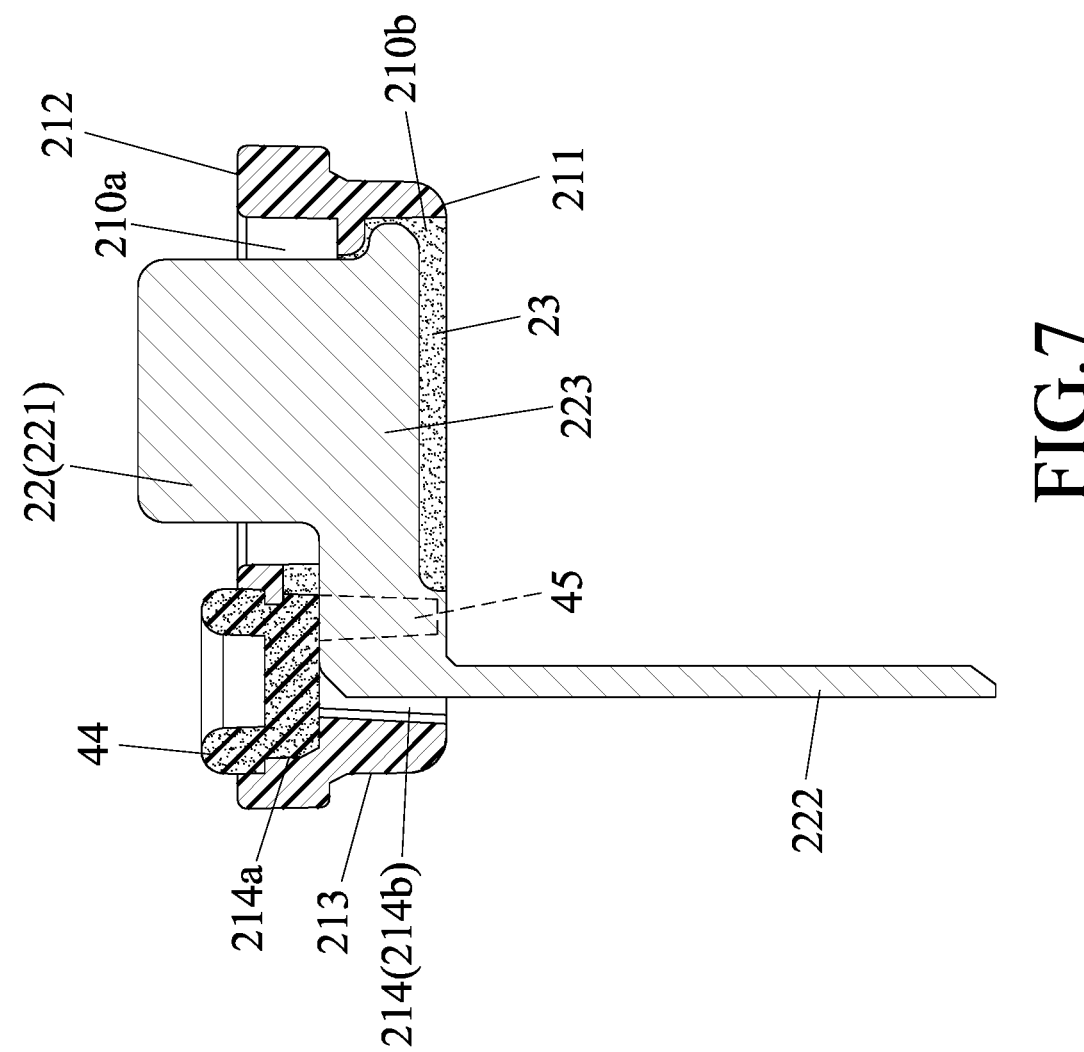

Referring to FIGS. 4, 6 and 7, the mounting space 210 of the mounting seat 21 has a cavity portion 210a that is open to the top surface 212, and a crevice portion 210b that is communicated to the cavity portion 210a in the direction of the first axis (D1). When the sensing member 22 is carried by the mounting seat 21, the signal output section 221 of the sensing member 22 is disposed in the cavity portion 210a and extends out of the top surface 212 of the mounting seat 21 along the direction of the first axis (D1). The extended section 223 of the sensing member 22 extends through the crevice portion 210b in the extending direction (D5), and then extends downwardly through the fitting hole 214 in the inserting direction (D4) to be connected to the sensing section 222. In order for the sensing member 22 to measure the analyte, the sensing section 222 subsequently extends through the bottom surface 116 of the base body 11 via the through hole 118 to be inserted underneath the skin surface of the host. That is, the sensing member 22 partially extends through the through hole 118 and is partially inserted underneath the skin surface of the host.

The fitting hole 214 of the mounting seat 21 and the through hole 118 of the base body 11 cooperatively define an implantation path (c) that extends in the inserting direction (D4) and that is for the inserting tool 9 (see FIG. 8) to removably extend therethrough, so as to insert the sensing section 222 of the sensing member 22 underneath the skin surface of the host.

Referring back to FIGS. 2 to 5, the transmitter 3 is removably covered to the base body 11 of the base 1 and connected to the biosensor 2 for receiving and outputting the physiological signal which is transmitted form the biosensor 2. The transmitter 3 includes a bottom portion 31, a top portion 32 that cooperates with the bottom portion 31 to define an outer casing 300 having an inner space 30 therein, a circuit board 33 that is disposed in the inner space 30, a battery 35 that is disposed in the inner space 30 and that is electrically connected to the circuit board 33, a connection port 36 that is connected to a bottom surface of the circuit board 33 and that extends outwardly from the inner space 30 toward the base body 11, and at least one second coupling structure 37 that is disposed on the bottom portion 31 and that corresponds in position to the at least one first coupling structure 12 of the base 1 so as to be detachably coupled with the first coupling structure 12 of the base body 11. In this embodiment, the bottom and top portions 31, 32 fittingly couple with each other, and the bottom portion 31 is proximate to the base body 11 and faces the top surface 115 of the bottom plate 111 of the base body 11

The bottom portion 31 includes a bottom surface 311, a top surface 312, a first groove 313 that indents from the bottom surface 311, and at least one second groove 314 that indents from the bottom surface 311 and that corresponds in position to the at least one first coupling structure 12. The first groove 313 is defined by a groove surrounding surface 315 that is connected to the bottom surface 311 and a groove bottom surface 316 that is connected to the groove surrounding surface 315. In this embodiment, the number of the second coupling structures 37 is two, and the number of the second groove 314 is two as well. When the transmitter 3 covers to the base 1 while the bottom portion 31 of the transmitter 3 faces the base 1, the bottom surface 311 abuts against the bottom plate 111 of the base body 11, the first groove 313 receives the inner surrounding wall 114 of the base body 11 and the biosensor 2 therein so that the sensing member 22 is coupled to the circuit board 33, and each of the second grooves 314 receives a respective pair of the first and second coupling structures 12, 37 therein, thereby reducing the overall thickness of the disclosure.

The circuit board 33 includes a plurality of electronic components for cooperating with the circuit board 33 to provide a signal transmission module (not shown) for receiving and sending the physiological signal measured by the sensing member 22. As the signal transmission module is well known in the art and may be internally rearranged to fit different needs, details thereof are omitted for the sake of brevity. Nevertheless, the electronic components may include a combination of a signal amplifier, an analog-digital signal converter, a processor, and a transmission unit.

Referring back to FIG. 5, the connection port 36 is connected to a bottom surface of the circuit board 33, protrudes downwardly in the direction of the first axis (D1) to be disposed in the first groove 313 of the bottom portion 31, and includes a socket 367 that is for the signal output section 221 of the sensing member 22 to be inserted thereinto to permit electric connection between the sensing member 22 and the circuit board 33. In this embodiment, the sensing member 22 is electrically connected to the circuit board 33 via a plurality of conducting members 364 disposed in the connection port 36. Specifically, the conducting members 364 are helical springs, respectively abut along a radial direction thereof against a plurality of electrical contacts (not shown) of the circuit board 33, and abut along the radial direction thereof against a plurality of the outputs 226 of the electrodes (see FIG. 6) on the signal output section 221 of the sensing member 22.

Referring back to FIGS. 3 and 5, the second coupling structures 37 are configured as grooves respectively disposed in the second grooves 314, correspond in position and in shape to the first coupling structures 12. When the transmitter 3 covers to the base body 11 of the base 1 while the bottom portion 31 of the transmitter 3 faces the top surface 115 of the bottom plate 111 of the base body 11, the first and second coupling structures 12, 37 are coupled to each other. To separate the transmitter 3 from the base 1, the first and second coupling structures 12, 37 are uncoupled to each other by applying an external force thereto.

It should be noted that, in this embodiment, the user may use his/her fingers or other disassembly tools (not shown) to apply the external force through the openings 117 to push against the first coupling structures 12, the second coupling structures 37, or a location where the first and second coupling structures 12, 37 couple to each other so as to separate the coupling structures. In other embodiments, the openings 117 may be omitted, and the base 1 is designed to be able to bend when the external force is applied thereto to separate the coupling structures. Nevertheless, some embodiments may have both of the abovementioned features to separate the coupling structures, and are not restricted to as such.

Referring back to FIG. 2, the base 1, the biosensor 2, and the transmitter 3 are separated from one another before use, and are coupled to one another to be mounted to the skin surface of the host. Referring back to FIG. 8, during the assembling, the base 1 and the biosensor 2 are coupled to the insertion device (not shown), the sensing section 222 of the sensing member 22 is carried by the insertion tool 9 of the insertion device to extend through the fitting hole 214 of the mounting seat 21 in the inserting direction (D4), and the base body 11 is attached to the skin surface via the adhesive pad 16. Then, as the sensing section 222 of the sensing member 22 is carried by the insertion tool 9 to extend through the through hole 118 of base body 11 and subsequently inserted underneath the skin surface of the host, the mounting seat 21 of the biosensor 2 is mounted to the mounting groove 113 of the base body 11. Referring back to FIG. 9, after the sensing section 222 of the sensing member 22 is inserted underneath the skin surface of the host, the insertion tool 9 is drawn out from the host so that the insertion device is separated from the base 1 and the biosensor 2, while the base 1 and the biosensor 2 remain coupled to one another. Lastly, referring back to FIGS. 4 and 5, to finish the assembling, the transmitter 3 covers to the base body 11 so that the first and second coupling structures 12, 37 are driven by the external force to be coupled to each other, while the signal output section 221 of the sensing member 22 is inserted into the connection port 36 via the socket 367 in the direction of the first axis (D1).

Referring back to FIGS. 4 and 5, since the base 1, the biosensor 2, and the transmitter 3 are all removable components of the physiological signal monitoring device, and since the insertion tool 9 extends through both the fitting hole 214 of the mounting seat 21 and the through hole 118 of the base 1 during the insertion process, internal components of the physiological signal monitoring device, such as the sensing member 22 of the biosensor 2 and the components disposed in the inner space 30 of the transmitter 3, are susceptible to leakage of external liquid thereinto. The body and external liquids, such as blood, may flow toward the inner space 30 of the transmitter 3 via a first liquid leakage pathway (a) and the implantation path (c), and may flow toward the signal output section 221 of the sensing member 22 via a fluid pathway (d) (see FIG. 4). Furthermore, the external liquid, such as contaminated liquid, may flow from a second liquid leakage pathway (b) toward the implantation path (c) through the first liquid leakage pathway (a) to contaminate the wound on the skin surface as well. Specifically, the first liquid leakage pathway (a) is cooperatively defined by the through hole 118 and a gap that is formed between the base 1 and the mounting seat 21, and that extends toward where the sensing member 22 is coupled to the transmitter 3; the second liquid leakage pathway (b) is defined by a gap that is formed between the base 1 and the transmitter 3 and that extends inwardly from an outer periphery of the transmitter 3 toward where the sensing member 22 is coupled to the transmitter 3; the implantation path (c) is defined by the through hole 118 and the fitting hole 214 and extends toward where the sensing member 22 is coupled to the transmitter 3. To prevent the internal components of the transmitter 3 from damage and even the infection of the wound, the physiological signal monitoring device further includes a sealing unit 4 for sealing the abovementioned liquid leakage pathways.

Referring back to FIGS. 3 to 5, the sealing unit 4 includes a first sealing member 42, a second sealing member 41, a third sealing member 48, a sixth sealing member 49, an urging module 47, and a blocking member 45. In general, the first sealing member 42 is clamped between the mounting seat 21 of the biosensor 2 and the bottom portion 31 of the transmitter 3 for sealing the first liquid leakage pathway (a); the second sealing member 41 is clamped between the base 1 and the transmitter 3 for sealing the second liquid leakage pathway (b); the third sealing member 48 is clamped between an inner peripheral surface of the inner surrounding wall 114 of the base 1 and the outer surrounding surface 213 of the mounting seat 21 for sealing the first liquid leakage pathway (a); and the urging module 47 is disposed between the bottom portion 31 of the transmitter 3 and the fitting hole 214 of the mounting seat 21 and seals a top portion 214*a* of the fitting hole 214 for sealing the implantation path (c). Detailed implementation of the abovementioned components of the sealing unit 4 is as follows.

The first sealing member 42 is clamped between the outer surrounding surface 213 of the mounting seat 21 and a groove surrounding surface 315 of the first groove 313 for sealing the first liquid leakage pathway (a). In this embodiment, the first sealing member 42 further abuts against an upper end of the inner surrounding wall 114 of the base 1 to simultaneously seal the first and second liquid leakage pathways (a, b).

As such, the first sealing member 42 of this embodiment is permitted to prevent leakage of the body liquid (especially blood) toward the gap between the groove bottom surface 316 (see FIG. 3) of the transmitter 3 and the top surface 212 of the mounting seat 21 sequentially from the through hole 118 and a gap between the base body 11 and the mounting seat 21, and to prevent the body liquid out of the physiological signal monitoring device sequentially through the through hole 118 and the first and second liquid leakage pathways (a, b) thus to scare the user. In the meanwhile, the first sealing member 42 further prevents the leakage of the external liquid (especially contaminated liquid) into the inner space 30 of the transmitter 3 through the outer surrounding wall 112 of the base 1 and the top portion 32 of the transmitter 3, the gap between the groove bottom surface 316 (see FIG. 3) of the transmitter 3 and the top surface 212 of the mounting seat 21 and subsequently through the socket 367 of the connection port 36, and to prevent leakage of the contaminated liquid to contact and infect the wound sequentially from the second liquid leakage pathway (b), the first liquid leakage pathway (a) and the through hole 118.

The second sealing member 41 is clamped between an outer peripheral surface of the inner surrounding wall 114 of the base 1 and the groove surrounding surface 315 of the first groove 313 of the transmitter 3 to prevent leakage of the external liquid (especially contaminated liquid) into the inner space 30 of the transmitter 3 from the gap between the outer surrounding wall 112 of the base body 11 and the top portion 32 of the transmitter 3 through a gap between the groove bottom surface 316 of the transmitter 3 and the top surface 212 of the mounting seat 21 and subsequently through the socket 367 of the connection port 36. On the other hands, the body liquid (especially blood) coming out of the wound is prevented from leaking out of the physiological signal monitoring device from the through hole 118 of the base 1 through a gap between the mounting seat 21 and the base body 11 (also noted as the first liquid leakage pathway (a)) and subsequently through the second liquid leakage pathway (b).

The third sealing member 48 is clamped between an inner peripheral surface of the inner surrounding wall 114 of the base and the outer surrounding surface 213 of the mounting seat 21 for sealing the first liquid leakage pathway (a) alongside the first sealing member 42 to prevent leakage of the body liquid (especially blood) into the gap between the groove bottom surface 316 of the transmitter 3 and the top surface 212 of the mounting seat 21 from the through hole 118 of the base body 11 through the gap formed between the base body 11 and the mounting seat 21. In addition, the third sealing member 48 is elastic, and the outer surrounding surface 213 of the mounting seat 21 tightly abuts against the third sealing member 48 for the mounting seat 21 to be fixedly mounted to the mounting groove 113 of the base 1. It should be noted that, in this embodiment, as the third sealing member 48 is used for fixedly mounting the mounting seat 21 to the mounting groove 113, in comparison to a conventional physiological signal monitoring device in which a base body 11 thereof is formed with holes and uses sealing members to fixedly mount a biosensor 2, the fluid-tightness of the physiological signal monitoring device of this embodiment is relatively superior.

The sixth sealing member 49 surrounds the inner surrounding wall 114 of the base 1, and is clamped between the top surface 115 of the bottom plate 111 and the bottom portion 31 of the transmitter 3 for sealing the second liquid leakage pathway (b) alongside the second sealing member 41. In should be noted that, the sixth sealing member 49 acts as a first defensive measure against leakage of the external liquid (especially contaminated liquid) through the second liquid leakage pathway (b). The external liquid can be effectually prevented from entering central portion of the physiological signal monitoring device (the mounting groove 113, the sensing member 22 in the mounting seat 21 and the socket 367 of the connection port 36), and to prolong service lives of the second and first sealing members 41, 42.

By evaluating the components of the sealing unit 4 collectively, the sixth sealing member 49 acts as the first defensive measure, the second sealing member 41 acts as the second defensive measure, and the first sealing member 42 acts as the third defensive measure against leakage of the external liquid (especially contaminated liquid) from entering the device. In addition, the above sealing members further prevents the external liquid from coming into contact with the wound on the skin surface through the first liquid leakage pathway (a) and the trough hole 118. In terms of preventing leakage of the body liquid (especially blood) from the wound to the transmitter 3 through the first liquid leakage pathway (a), the third sealing member 48 acts as the first defensive measure, and the first sealing member 42 acts as the second defensive measure. Furthermore, the blood can be further prevented from exiting the physiological signal monitoring device through the second liquid leakage pathway (b).

Figure 9:
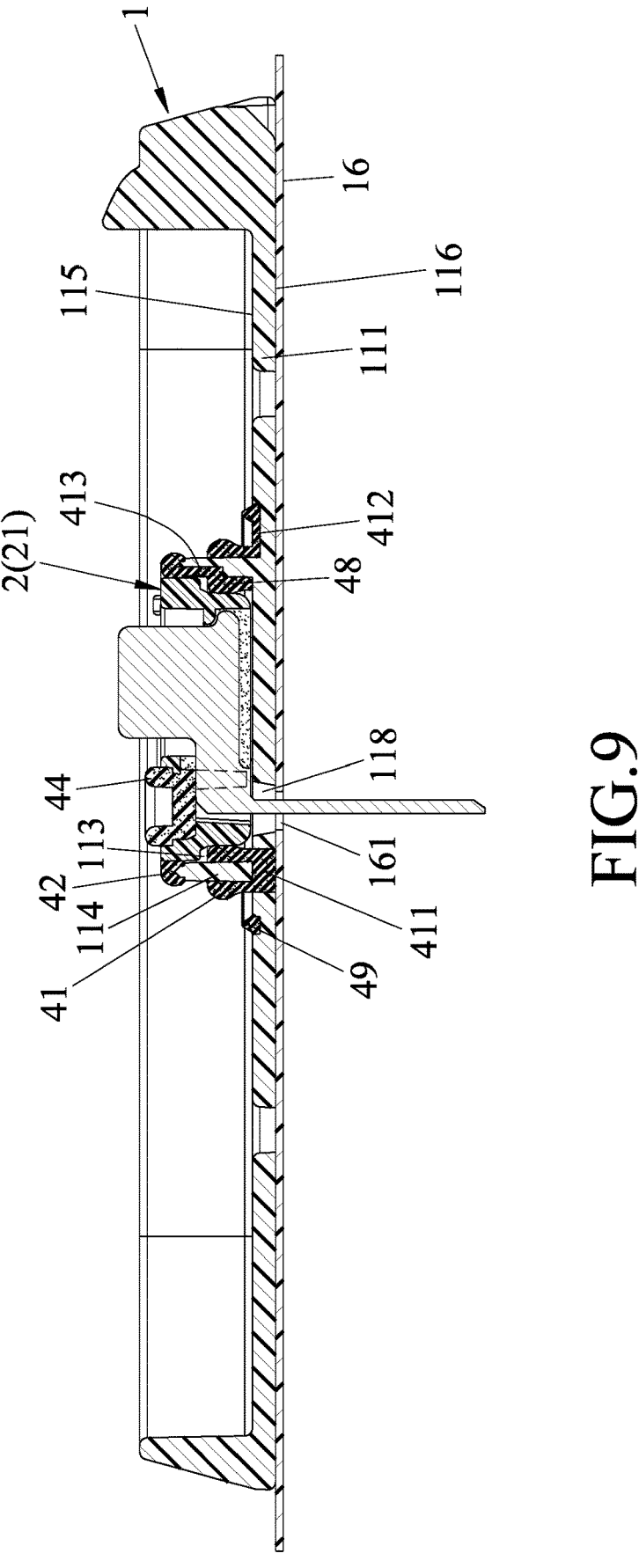

Referring to FIG. 9, in this embodiment, the first, second, third, and sixth sealing members 42, 41, 48, 49 are made of elastic materials such as rubbers, are formed as a single piece, and are mounted to the base 1, but may be made of other elastic materials capable of preventing fluid leakage in other embodiments. Specifically, the abovementioned sealing members are injection molded to be formed as a single piece coupled to the base body 11. In details, an elastic material is injected to surround the outer peripheral surface of the inner surrounding wall 114 of the base body 11 to form the second sealing member 41 at first. Then, a portion of the elastic material of the second sealing member 41 will extend downwardly to be embedded into the bottom plate 111 and form a connecting portion 411, and the connecting portion 411 will subsequently extend upwardly to surround the inner peripheral surface of the inner surrounding wall 114 so as to form the third sealing member 48. In the meanwhile, a portion of the elastic material of the second sealing member 41 also extends along the top surface 115 of the bottom plate 111 and towards the outside of the mounting groove 113 for forming another connecting portion 412, which will surround the mounting groove 113 to form the sixth sealing member 49. A portion of the elastic material of the third sealing member 48 also extends upwardly and along the inner peripheral surface of the inner surrounding wall 114 to form further another connecting portion 413, which will enwrap the upper end of the inner surrounding wall 114 to form the first sealing member 42. The connecting portion 411 may be flush with or protrude from the bottom surface 116 of the bottom plate 111. However, the abovementioned sealing members may be separate pieces mounted to the base 1.

In addition, the connecting portion 411 interconnecting the second and third sealing members 41, 48 extends through the bottom plate 111 to abut against the adhesive pad 16/or the skin surface of the host. Similar to the waterproof portion 162 of the adhesive pad 16, the connecting portion 411 can block the contaminated liquid absorbed in the adhesive pad 16 and prevent the contaminated liquid from moving toward the pad hole 161 to contact the wound on the skin surface. It should be noted that, it is possible to omit one of the waterproof portion 162 of the adhesive pad 16 and the connecting portion 411 of the sealing unit without reducing the effectiveness of leakage prevention.

Referring to FIGS. 4 and 7, the urging module 47 seals the top portion 214a of the fitting hole 214, and has a urging member 46 that is disposed at the bottom portion 31 of the transmitter 3, that corresponds in position to the fitting hole 214, and that is tightly coupled to the top portion 214a of the fitting hole 214. Specifically, the urging member 46 is disposed on the groove bottom surface 316 of the first groove 313 of the transmitter 3 (see FIG. 3), and the urging module further has a fourth sealing member 44 that is mounted to the top portion 214a of the fitting hole 214 and that is tightly coupled to the urging member 46 for sealing the implantation path (c) and for preventing the body liquid (especially blood) from entering the inner space 30 of the transmitter 3 through the socket 367 of the connection port 36. The fourth sealing member 44 is made of an elastic material such as rubbers, and the urging member 46 and the bottom portion 31 of the transmitter 3 are formed as a single piece of non-elastic material that is harder than that of the fourth sealing member 44. The fourth sealing member 44 is cooperated in shape with the urging member 46 so as to enforce the seal of the implantation path (c). In addition, since the fourth sealing member 44 is elastic, it maintains fluid-tightness of the physiological signal monitoring device after the insertion tool 9 (see FIG. 8) is removed. In addition, in this embodiment, the fourth sealing member 44 protrudes upwardly from the top surface 212 of the mounting seat 21, and the top surface 212 of the mounting seat 21 is further formed with two resilient members 50 (see FIG. 6) protruded therefrom for ensuring stable contact of the mounting seat 21 with the transmitter 3.

Overall, when the user inserts the sensing member 22 beneath the skin surface of the host via an insertion tool 9 after the base 1 has been attached to the skin surface, the first and/or third sealing member(s) 42, 48 mounted to the base 1 in conjunction with the fourth sealing member 44 mounted to the mounting seat 21 seal all of the body liquid bleeding out of the wound during the insertion process within the gap between the base 1 and the biosensor 2 or inside the mounting seat 21 of the biosensor 2, so that the body liquid do not leak out of the physiological signal monitoring device to scare the user and that the time the user is required to wait to mount the transmitter 3 to the base 1 after the insertion process is also reduced.

Also, referring back to FIGS. 4 and 7, the blocking member 45 is disposed for blocking the communication between the fitting hole 214 and the mounting space 210 along the extending direction (D5), and is made of an elastic material that permits the extended section 223 of the sensing member 22 to extend therethrough and to tightly abut thereagainst, so that body liquid is prevented from leaking into the mounting space 210 from the fitting hole 214 through the fluid pathway (d) to be in contact with the signal output section 221 of the sensing member 22. Preferably, both lateral sides of the extended section 223 of the sensing member 22 are permitted to be clamped by the blocking member 45 to stably position the sensing member 22 relative to the mounting seat 21. In addition, the mounting seat 21 of the biosensor 2 is permitted to be further sealed at its bottom with a glue 23 to block the body liquid from flowing through both the first liquid leakage pathway (a) and the fluid pathway (d).

Many components of the base body 11, the biosensor 2, and the transmitter 3 fittingly engage with one another along the direction of the first axis (D1) to minimize the overall volume of the physiological signal monitoring device. Referring back to FIGS. 3 and 4, in this embodiment, when the base 1 and the transmitter 3 are coupled to each other, the first groove 313 of the bottom portion 31 of the transmitter 3 cooperates with the base 1 to define a mounting space 100 for receiving the mounting seat 21 of the biosensor 2 therein, such that physical configuration of the electric connection between the connection port 36 and the biosensor 2 is confined within the first groove 31. In addition, the first groove 313 divides the inner space 30 into two sections along the direction of the second axis (D2) that respectively receive the battery 35 and electric components (not shown) of the circuit board 33. By distributing the abovementioned components evenly within the inner space 30, the transmitter 3 may be designed to be more compact with smaller thickness in the direction of the first axis (D1).

Figure 21:
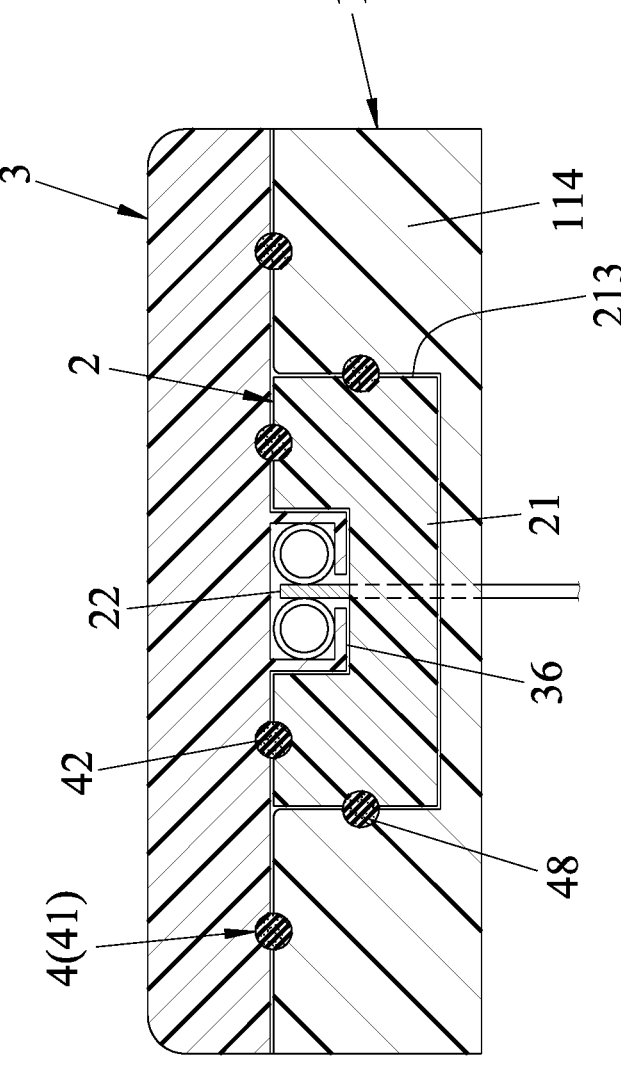
FIG. 21 is a schematic sectional view of a modification of the physiological signal monitoring device.
Figure 22:
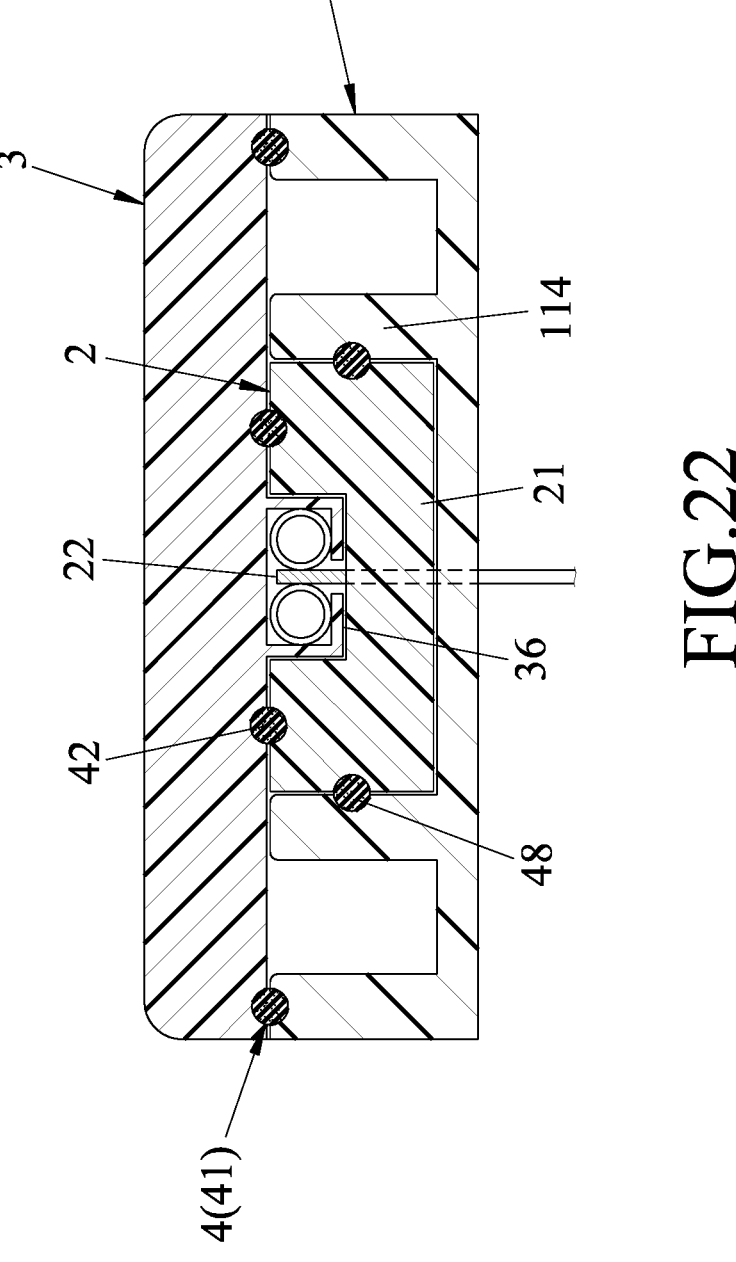
FIG. 22 is a schematic sectional view of another modification of the physiological signal monitoring device.

However, in other embodiments, the mounting seat 21 of the biosensor 2 is complemented in structure with at least a part of the bottom portion 31 of the transmitter 3. For example, as shown in FIGS. 21 and 22, one of the bottom portion 31 of the transmitter 3 and the mounting seat 21 of the biosensor 2 is formed with a groove that receives at least a portion of the other one of the mounting seat 21 and the bottom portion 31 of the transmitter 3. Referring to FIG. 22, the mounting seat 21 is formed with a groove that receives the connection port 36 of the transmitter 3, and the first groove 313 is omitted. In this modification, the sealing unit 4 is capable for preventing leakage as well: the first sealing member 42 is clamped between the mounting seat 21 of the biosensor 2 and the bottom portion 31 of the transmitter 3 for sealing the first liquid leakage pathway (a); the second sealing member 41 is clamped between the base 1 and the transmitter 3 for sealing the second liquid leakage pathway (b), and the third sealing member 48 is clamped between the inner peripheral surface of the inner surrounding wall 114 of the base 1 and the outer surrounding surface 213 of the mounting seat 21 for sealing the first liquid leakage pathway (a).

Referring back to FIGS. 2 and 5, as the physiological signal monitoring device is meant to measure microcurrent on the scales of nanoampere (nA), in addition to maintaining the fluid-tightness, the physiological signal monitoring device further includes a desiccant 5 that is mounted anywhere in the mounting space 100, so that the biosensor 2 is remained to be in low humidity to ensure proper measurement. In this embodiment, the mounting space 100 is disposed between the first groove 313 of the bottom portion 31 of the transmitter 3 and the bottom plate 111 of the base 1, the top surface 212 of the mounting seat 21 is formed with two humidity grooves 217 (see FIG. 2) for storing two of the desiccants 5 therein, and the sensing member 22 is connected to the transmitter 3 in the mounting space 100.

However, in a modification of the embodiment, the humidity grooves 217 are omitted, and the groove bottom surface 316 of the transmitter 3 is formed with two humidity grooves (not shown) for storing the desiccants 5 therein. In other embodiments, the mounting seat 21 itself may be partially made of the desiccants 5 during the injection molding process, such that the biosensor 2 as a whole remained to be in low humidity.

Referring to FIGS. 10 to 14, a second embodiment of the physiological signal monitoring device is similar to that of the first embodiment, with difference as follows.

Figure 12:
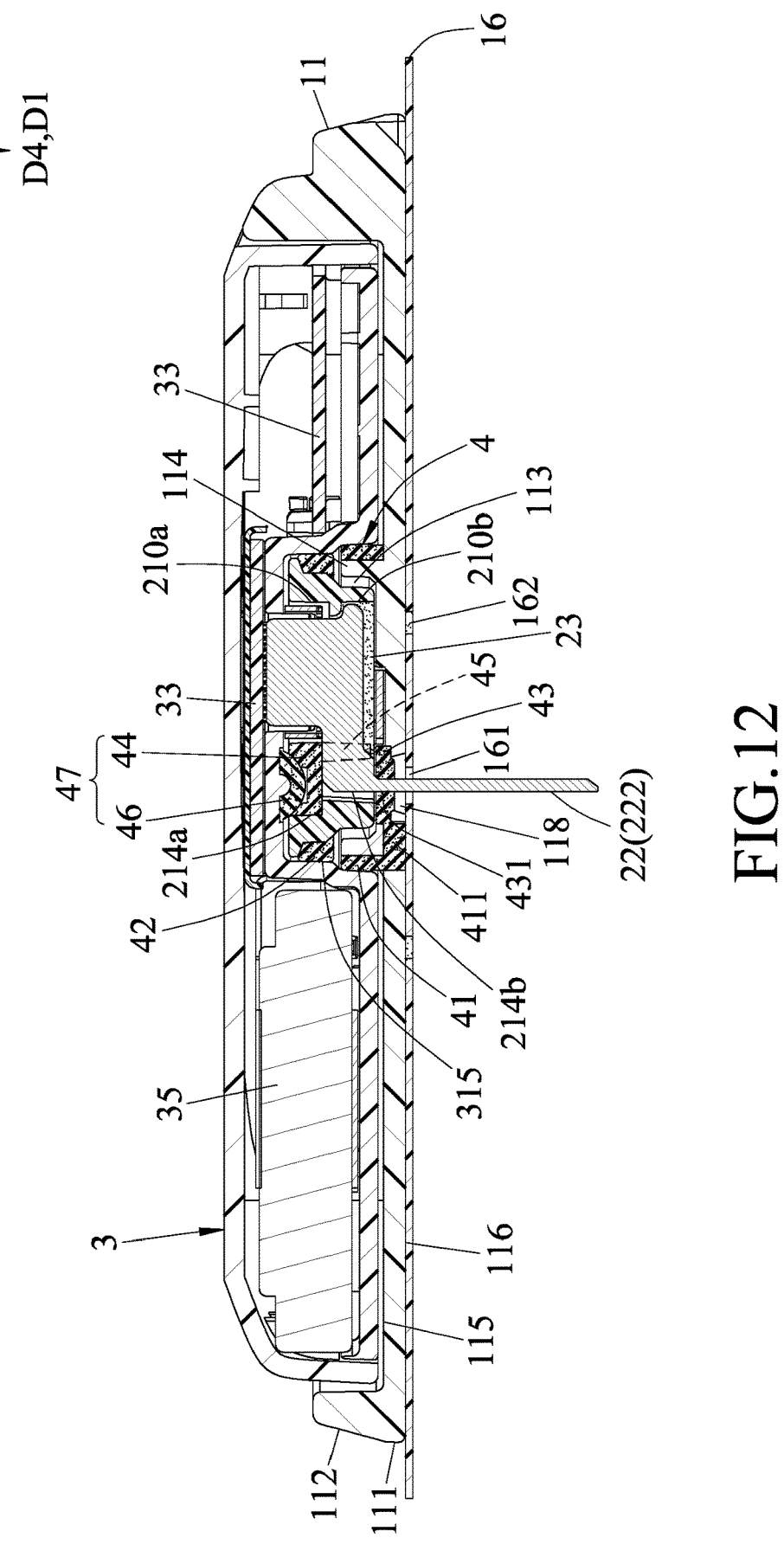
FIG. 12 is a sectional view of the second embodiment.
Figure 13:
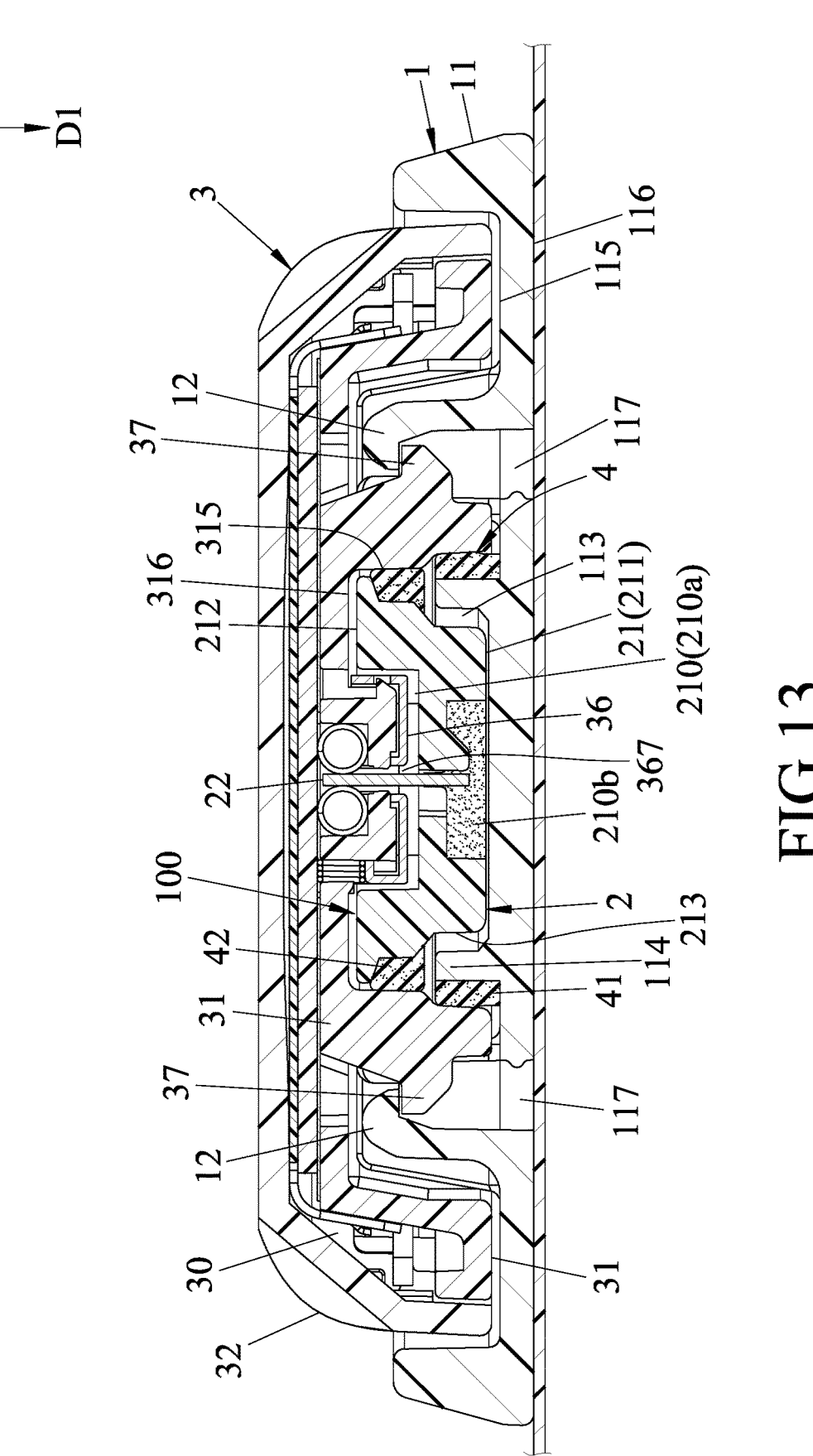
FIG. 13 is another sectional view of the second embodiment.
Figure 14:
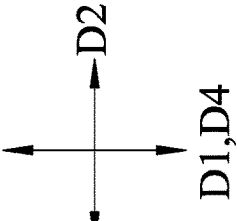
FIG. 14 is a sectional view of the base and the biosensor of the second embodiment, illustrating the biosensor after being coupled to the base via the insertion tool.
Figure 14:
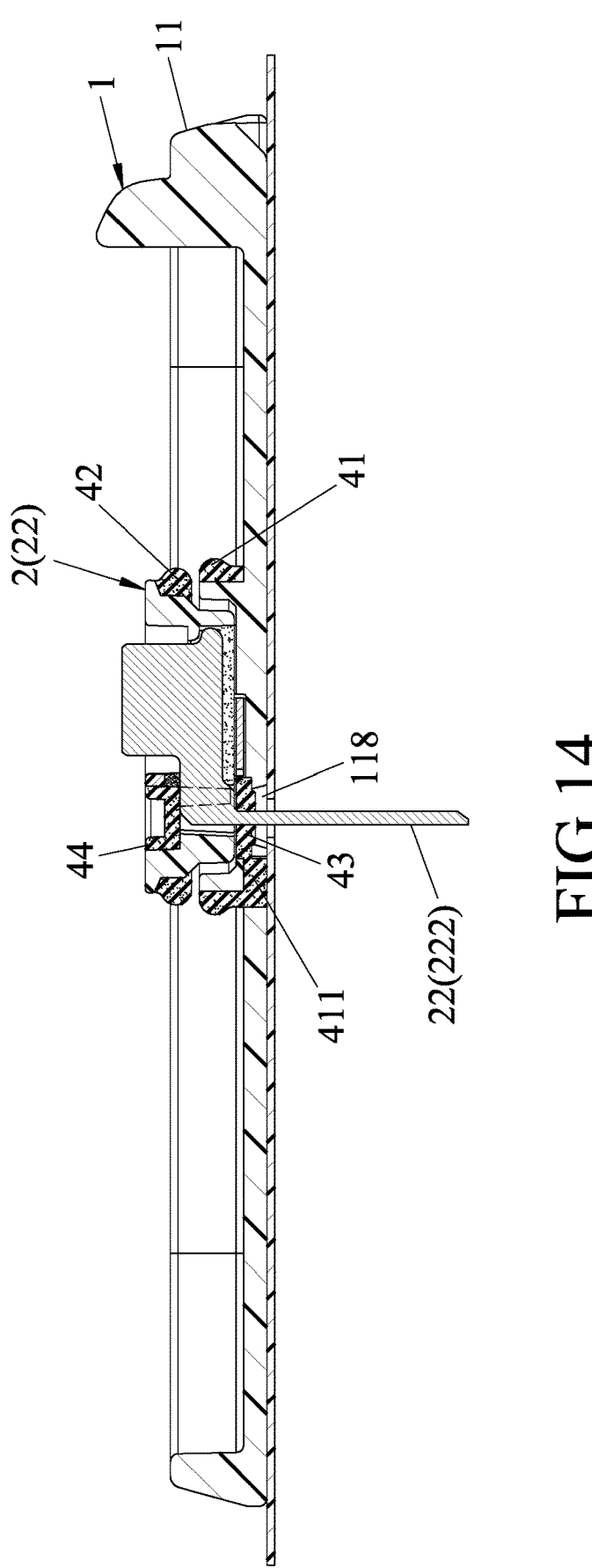

Referring specifically to FIG. 12, the third sealing member 48 of the sealing unit 4 is omitted, and the sealing unit 4 further includes a fifth sealing member 43 that is mounted to the base 1 and that seals the through hole 118. In this embodiment, the fifth sealing member 43 seals an end of the through hole 118 of the base body 11 distal from the host, and is formed with a premade hole 431 for the insertion tool 9 to pass therethrough so as to reduce the resistance of the implantation. In other embodiments, the fifth sealing member 43 can be directly punctured therethrough by the insertion tool 9 and guide the sensing member 22 so that the premade hole 431 can be omitted. In such embodiments, the fifth sealing member 43 is made of an elastic material such as rubber, and abuts against the sensing member 22 to fluid-tightly seals the physiological signal monitoring device after the insertion tool 9 is drawn out. In addition, as the fifth sealing member 43 seals an end of the through hole 118 of the base body 11 distal from the host, the through hole 118 itself is permitted for containing the blood released from the host, such that the blood is given enough open space to relieve pressure, so that the blood would not be able to flow through any potential gap between the fifth sealing member 43 and the sensing member 22 due to high pressure.

Figure 10:
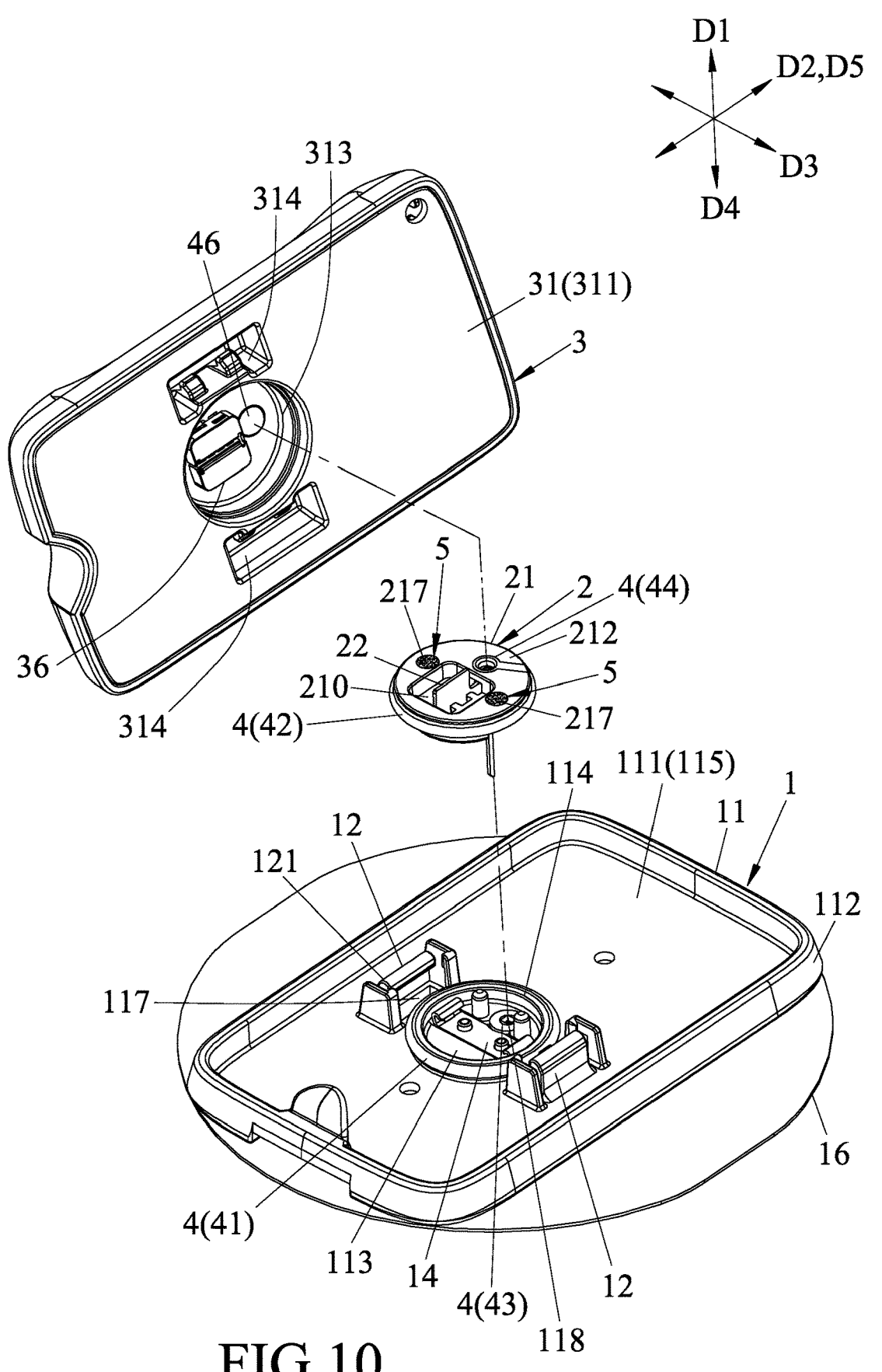
FIG. 10 is a perspective view of a second embodiment of the physiological signal monitoring device.
Figure 11:
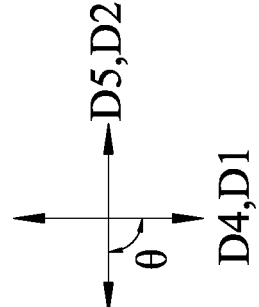
FIG. 11 is a sectional view of the biosensor of the second embodiment.

Furthermore, referring specifically to FIGS. 10 and 12, the second and fifth sealing members 41, 43 of this embodiment are injection molded to be formed as a single piece coupled to the base body 11, but may be separate pieces in other embodiments. Specifically, in this embodiment, an elastic material is injected to surround the outer peripheral surface of the inner surrounding wall 114 of the base body 11 to form the first sealing member 42 at first. Then, a portion of the elastic material of the first sealing member 42 will extend downwardly to be embedded into the bottom plate 111 and form a connecting portion 411, and the connecting portion 411 will subsequently extend upwardly to surround the through hole 118 so as to form the fifth sealing member 43. The connecting portion 411 may be flush with or protrude from the bottom surface 116 of the bottom plate 111. Similar to the waterproof portion 162 of the adhesive pad 16, the connecting portion 411 can block the contaminated liquid absorbed in the adhesive pad 16 and prevent the contaminated liquid from moving toward the pad hole 161 to contact the wound on the skin surface. It should be noted that, it is possible to omit one of the waterproof portion 162 of the adhesive pad 16 and the connecting portion 411 of the sealing unit 4 without reducing the effectiveness of leakage prevention. In other embodiments, the connecting portion 411 also can be formed by extend a portion of the fifth sealing member 43 to surround the opposite two surfaces of the through hole 118 and even extend to the surface of the pad hole 161 for being against the skin surface of the host. However, the waterproof portion 162 can be omitted in such embodiments.

Furthermore, referring back to FIGS. 11, 13, and 14, in the second embodiment, the first sealing member 42, in addition of being clamped between the outer surrounding surface 213 of the mounting seat 21 and the groove surrounding surface 315 of the first groove 313 of the transmitter 3, is mounted to the outer surrounding surface 213 of the mounting seat 21 and does not abut against the upper end of the inner surrounding wall 114 of the base 1. As such, in terms of leakage prevention, the second sealing member 41 acts as the first defensive measure, and the first sealing member 42 acts as the second defensive measure against leakage of the external liquid (especially contaminated liquid) from entering the inner space of the transmitter 3 through the second liquid leakage pathway (b). In terms of preventing leakage of the body liquid, such as blood, from the wound to the transmitter 3 through the first liquid leakage pathway (a), the fifth sealing member 43 acts as the first defensive measure, and the first sealing member 42 acts as the second defensive measure. Furthermore, the second sealing member 41 prevents the body fluid (especially blood) from exiting the physiological signal monitoring device through the second liquid leakage pathway (b), while the fifth sealing member 43 prevents the external liquid (especially contaminated liquid) from coming into contact with the wound on the skin surface through the first liquid leakage pathway (a).

Referring specifically to FIG. 12, in this embodiment, the urging member 46 of the urging module 47 is a protrusion made of a soft material (such as rubbers), the fourth sealing member 44 is formed with a groove and is made of a soft material (such as rubbers) for the urging member 46 to be tightly coupled thereto to seal the implantation path (c).

Figure 15:
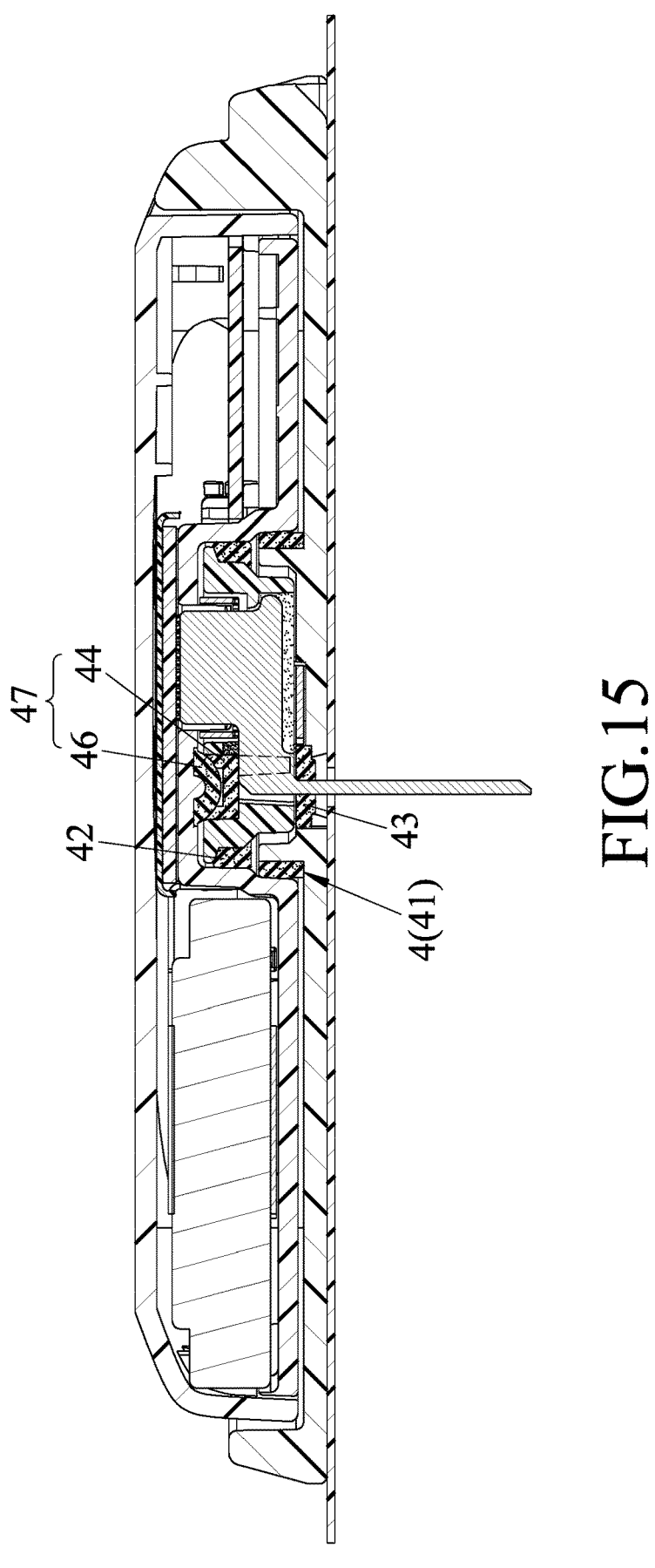
FIG. 15 is a sectional view of a modification of the second embodiment.

It should be noted that, the first and fourth sealing members 42, 44 may be formed as a single piece coupled to the base 1, and the second and fifth sealing members 41, 43 may be formed as a single piece coupled to the mounting seat 21 of the biosensor 2, but they may all be separate pieces in other embodiments. For example, referring to FIG. 15, in a modification of the second embodiment, the second and fifth sealing members 41, 43 are separate pieces and are not connected to one another directly In addition, the first and second sealing members 42, 41 are O-rings, preferably the type of O-rings with triangular cross-section. However, the disclosure is not restricted to be as such. Lastly, in the second embodiment, the mounting groove 113 of the base 1 includes a coupling member 14 (see FIG. 10) that engages with a bottom end of the mounting seat 21.

Figure 16:
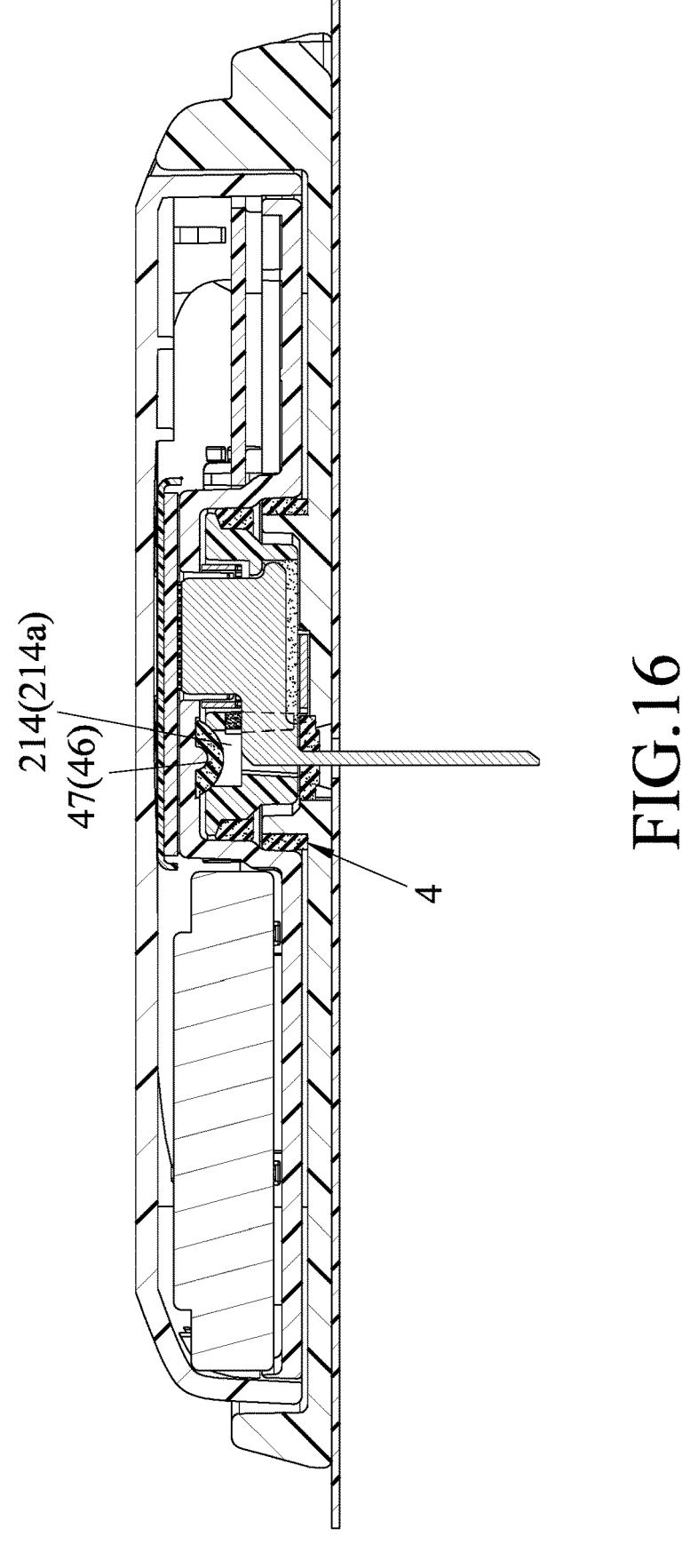
FIG. 16 is a sectional view of a third embodiment of the physiological signal monitoring device.

Referring to FIG. 16, a third embodiment of the physiological signal monitoring device is similar to that of the second embodiment, with difference as follows: the fourth sealing member 44 of the urging module 47 is omitted, and the urging member 46 is tightly coupled to the top portion 214a of the fitting hole 214 directly to seal the fitting hole 214. In addition, as the urging member 46 is made of a rubber material, it is easily deformable in accordance to fittingly engage the top portion 214a of the fitting hole 214, thereby securely sealing the implantation path (c).

Figure 17:
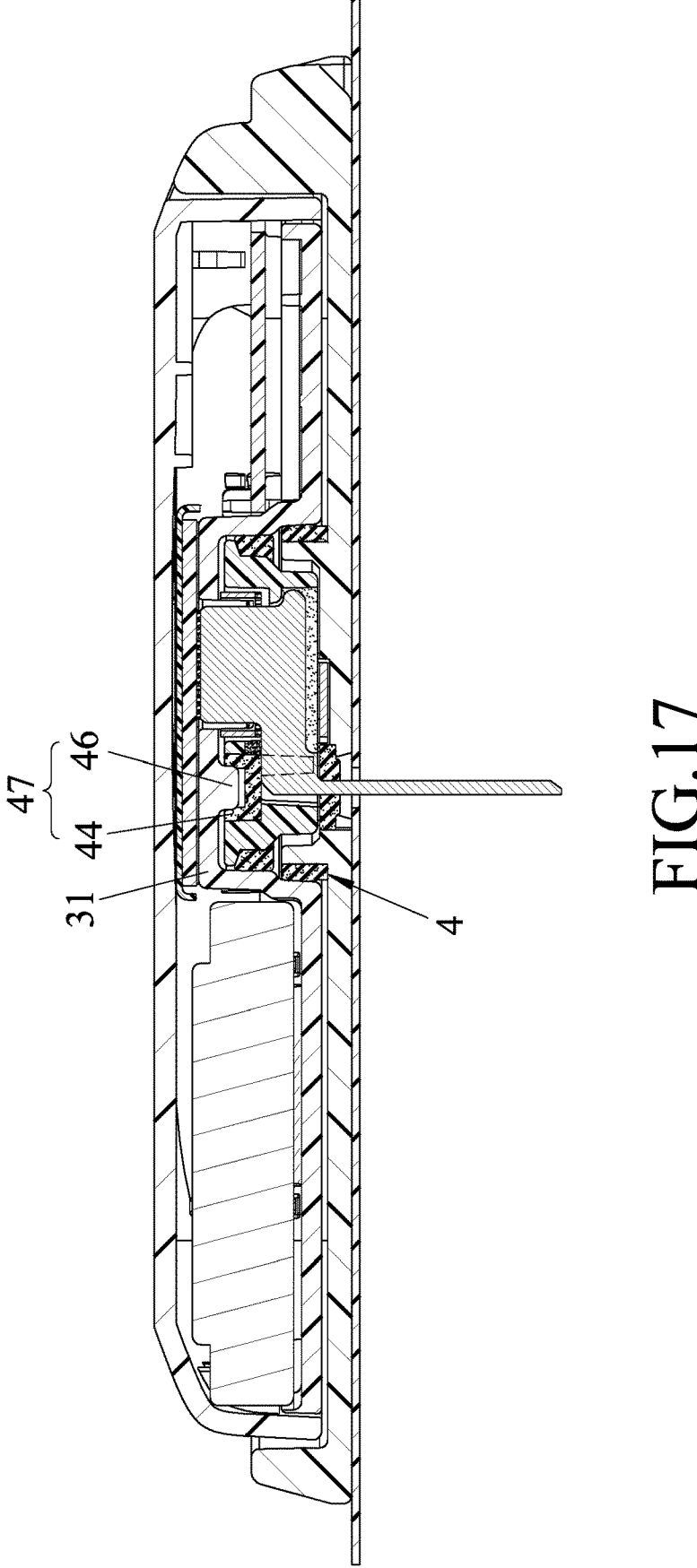
FIG. 17 is a sectional view of a fourth embodiment of the physiological signal monitoring device.

Referring to FIG. 17, a fourth embodiment of the physiological signal monitoring device is similar to that of the second embodiment, with difference as follows: the urging member 46 of the sealing unit 4 and the bottom casing 31 of the transmitter 3 are formed as a single piece of non-elastic material, and are tightly coupled to the groove formed on top of the fourth sealing member 44 to thereby securely sealing the implantation path (c).

Figure 18:
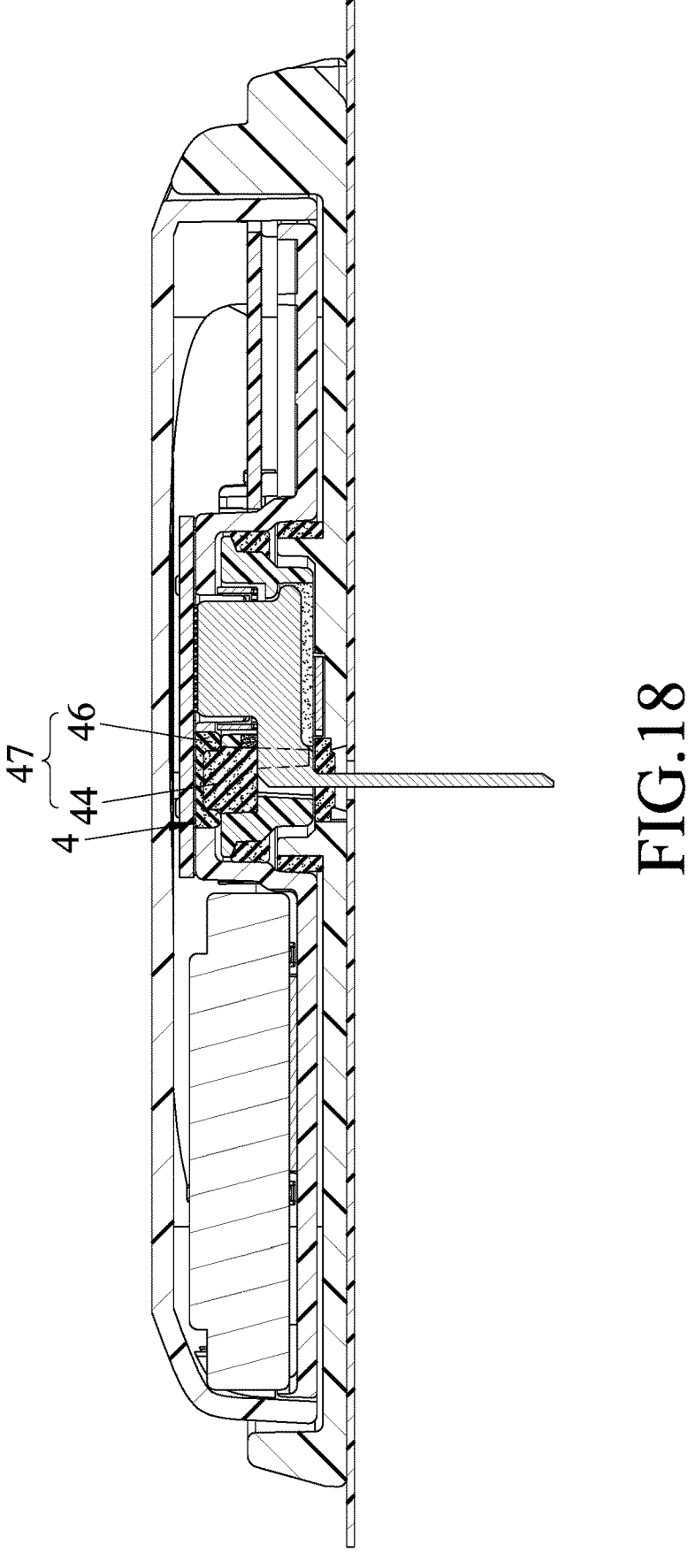
FIG. 18 is a sectional view of a fifth embodiment of the physiological signal monitoring device.

Referring to FIG. 18, a fifth embodiment of the physiological signal monitoring device is similar to that of the second embodiment, with difference as follows: the groove on the fourth sealing member 44 is omitted, and the urging member 46 is indented with a groove in a bottom surface thereof for the fourth sealing member 44 to be tightly coupled thereto instead. In other words, the fourth sealing member 44 formed as a protrusion that is permitted to extend into the groove on the bottom surface of the urging member 46. As both the fourth sealing member 44 and the urging member 46 are made of rubber materials, they are easily deformable to tightly couple with each other, thereby sealing the implantation path (c).

Figure 19:
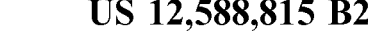
FIG. 19 is a sectional view of a sixth embodiment of the physiological signal monitoring device.

Referring to FIG. 19, a sixth embodiment of the physiological signal monitoring device is similar to that of the fifth embodiment, with difference as follows: while the urging member 46 is still indented with a groove on the bottom surface thereof for the fourth sealing member 44 to be tightly coupled thereto, the urging member 46 of the sealing unit 4 and the bottom casing 31 of the transmitter 3 are formed as a single piece of hard material, and the fourth sealing member 44 is a protrusion made of a rubber material. As such, the fourth sealing member 44 is easily deformable to tightly couple to the groove formed beneath the urging member 46, thereby sealing the implantation path (c).

Figure 20:
FIG. 20 is a sectional view of a seventh embodiment of the physiological signal monitoring device.

Referring to FIG. 20, a seventh embodiment of the physiological signal monitoring device is similar to that of the second embodiment, with difference as follows: the first and second sealing member 42, 41 are formed as a single piece that is clamped among the outer surrounding surface 213 of the mounting seat 21, the inner surrounding wall 114 of the base body 11, and the groove surrounding surface 315 of the transmitter 3 for simultaneously sealing the first liquid leakage pathway (a) and the second liquid leakage pathway (b). In particular, only the first sealing member 42 is disposed between the mounting seat 21 and the groove surrounding surface 315. In the meanwhile, the first sealing member 42 is against the top of the inner surrounding wall 114 of the base 11 so as to prevent the blood and the contaminated liquid, respectively, from leaking into the transmitter 3 via the first liquid leakage pathway (a) and the second liquid leakage pathway (b).

Overall, the sealing unit 4 of the physiological signal monitoring device of this disclosure effectively prevent leakage of external liquid into the physiological signal monitoring device from damaging the internal components thereof or into the wound on the skin surface by traversing through the physiological signal monitoring device. In addition, the sealing unit 4 also blocks body liquid, such as blood, from contaminating the transmitter 3 or from exiting the physiological signal monitoring device from the wound on the skin surface through the physiological signal monitoring device. Accordingly, the fear of the user will be reduced during the assembling.

In addition to the embodiments described above, this disclosure further discloses a plurality of embodiments as defined by the claims, with each embodiment comprising the claim element(s) of the respective claim and the claim element(s) of any claim upon which the respective claim depends.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A physiological signal monitoring device comprising:
a base (1) that is adapted to be mounted to a skin surface of a host;
a biosensor (2) that is mounted to said base (1) and that includes
a mounting seat (21) having a bottom surface (211) and a top surface (212), and being formed with a fitting hole (214) that extends through said top and bottom surfaces (212, 211), and
a sensing member (22) carried by said mounting seat (21) and partially extending through said fitting hole (214), said sensing member (22) having a sensing section (222) that extends through a bottom portion (214*b*) of the fitting hole (214), said sensing section (222) being adapted to be partially inserted underneath the skin surface of the host for measuring at least one analyte of the host and to send a corresponding physiological signal, said fitting hole (214) of said mounting seat (21) being adapted for an insertion tool (9) to removably extend therethrough to guide said sensing member (22) to be partially inserted underneath the skin surface of the host;
a transmitter (3) that is removably mounted to said base (1), that is for receiving and transmitting the physiological signal, and that has a bottom portion (31) facing said base (1) when said transmitter (3) is mounted to said base (1) so as to allow said mounting seat (21) to be disposed between said base (1) and said transmitter (3) and to allow said sensing member (22) to be coupled to said transmitter (3); and
a sealing unit (4) that includes
an urging module (47) disposed between said bottom portion (31) of said transmitter (3) and said fitting hole (214) of said mounting seat (21), said urging module (47) having a fourth sealing member (44) that is mounted to a top portion (214*a*) of said fitting hole (214) and that is made of an elastic material, which is configured to be pierced by the insertion tool (9) during an insertion process and then block said fitting hole (214) to maintain fluid-tightness of said physiological signal monitoring device after the insertion tool (9) is removed therefrom and before said transmitter (3) is covered on said base (1) for sealing an implantation path (c),
wherein said urging module (47) further has an urging member (46) that is disposed at said bottom portion (31) of said transmitter (3), that corresponds in position to said fitting hole (214), and that is tightly coupled to said top portion (214*a*) of said fitting hole (214), and
wherein said fourth sealing member (44) is tightly coupled to said urging member (46) for sealing the implantation path (c).

2. The physiological signal monitoring device as claimed in claim 1, wherein said bottom portion (31) of said transmitter (3) has a first groove (313) which cooperates with said base (1) to define a mounting space (100) for receiving said mounting seat (21) of said biosensor (2) therein, said urging member (46) being disposed on a groove bottom surface (316) of said first groove (313).

3. The physiological signal monitoring device as claimed in claim 1, wherein said urging member (46) of said sealing unit (4) is a protrusion, said fourth sealing member (44) being formed with a groove for the urging member (46) to be tightly coupled thereto.

4. The physiological signal monitoring device as claimed in claim 1, wherein said urging member (46) of said sealing unit (4) is indented with a groove in a bottom surface thereof, said fourth sealing member (44) being formed as a protrusion that extends into said groove on said urging member (46) so as to be tightly coupled to said urging member (46).

5. The physiological signal monitoring device as claimed in claim 1, wherein said base (1) has a through hole (118), said fitting hole (214) of said mounting seat (21) and said through hole (118) of said base (1) cooperatively defining the implantation path (c) that is for the insertion tool (9) to removably extend therethrough so as to insert said sensing member (22) underneath the skin surface of the host.

6. The physiological signal monitoring device as claimed in claim 1, wherein:
said base (1) includes a bottom plate (111) that is adapted to be mounted to the skin surface of the host, and an inner surrounding wall (114) that protrudes from a top surface (115) of said bottom plate (111), said inner surrounding wall (114) and said bottom plate (111) cooperatively defining a mounting groove (113) therebetween, said mounting seat (21) of said biosensor (2) being mounted to said mounting groove (113) of said base (1); and
said sealing unit (4) further includes a third sealing member (48) that is clamped between an inner peripheral surface of said inner surrounding wall (114) of said base (1) and an outer surrounding surface (213) of said mounting seat (21) for sealing a first liquid leakage pathway (a).

7. The physiological signal monitoring device as claimed in claim 6, wherein:

said base (1) is formed with a through hole (118) that is communicated to said mounting groove (113), and that is for said sensing member (22) to partially extend therethrough so that said sensing member (22) is partially inserted underneath the skin surface of the host; and said through hole (118) and a gap, which is formed between said base (1) and said mounting seat (21) of said biosensor (2) and extending toward where said sensing member (22) is coupled to said transmitter (3), cooperatively define the first liquid leakage pathway (a).

8. A physiological signal monitoring device comprising:

a base (1) that includes a bottom plate (111) adapted to be mounted to a skin surface of a host, and an inner surrounding wall (114) that protrudes from a top surface (115) of said bottom plate (111), said inner surrounding wall (114) and said bottom plate (111) cooperatively defining a mounting groove (113) therebetween;

a biosensor (2) that is mounted to said base (1) and that includes a mounting seat (21) mounted to said mounting groove (113) of said base (1), and a sensing member (22) carried by said mounting seat (21), and adapted to be partially inserted underneath a skin surface of a host for measuring at least one analyte of the host and to send a corresponding physiological signal;

a transmitter (3) that is removably mounted to said base (1), that is for receiving and transmitting the physiological signal, and that has a bottom portion (31), said bottom portion (31) facing said base (1) when said transmitter (3) is mounted to said base (1) so as to allow said mounting seat (21) to be disposed between said base (1) and said transmitter (3) and to allow said sensing member (22) to be coupled to said transmitter (3); and a sealing unit (4) that includes a third sealing member (48) that is non-conductive and clamped between an inner peripheral surface of said inner surrounding wall (114) of said base (1) and an outer surrounding surface (213) of said mounting seat (21) for sealing a first liquid leakage pathway (a).

9. The physiological signal monitoring device as claimed in claim 8, wherein:

said base (1) is formed with a through hole (118) that is communicated to said mounting groove (113), and that is for said sensing member (22) to partially extend therethrough so that said sensing member (22) is partially inserted underneath the skin surface of the host; and said through hole (118) and a gap, which is formed between said base (1) and said mounting seat (21) of said biosensor (2) and extending toward where said sensing member (22) is coupled to said transmitter (3), cooperatively define the first liquid leakage pathway (a).

10. The physiological signal monitoring device as claimed in claim 8, wherein:

said mounting seat (21) of said biosensor (2) has a bottom surface (211) and a top surface (212), and is formed with a fitting hole (214) that extends through said top and bottom surfaces (212, 211), said fitting hole (214) being adapted for an insertion tool (9) to removably extend therethrough to guide said sensing member (22) to partially extend through said fitting hole (214) and be partially inserted underneath the skin surface of the host; and said sealing unit (4) further includes a fourth sealing member (44) that is mounted to a top portion (214a) of said fitting hole (214) for sealing an implantation path (c).

11. The physiological signal monitoring device as claimed in claim 10, wherein said fourth sealing member (44) is made of an elastic material.

12. The physiological signal monitoring device as claimed in claim 10, wherein said base (1) has a through hole (118), said fitting hole (214) of said mounting seat (21) and said through hole (118) of said base (1) cooperatively defining the implantation path (c) that is for the insertion tool (9) to removably extend therethrough so as to insert said sensing member (22) underneath the skin surface of the host.

13. The physiological signal monitoring device as claimed in claim 10, wherein said sealing unit (4) further includes an urging member (46) that is disposed at said bottom portion (31) of said transmitter (3), that corresponds in position to said fitting hole (214), and that is tightly coupled to said fourth sealing member (44) for sealing the implantation path (c).

14. A physiological signal monitoring device comprising:

a base (1) that includes a bottom plate (111) adapted to be mounted to a skin surface of a host, and an inner surrounding wall (114) that protrudes from a top surface (115) of said bottom plate (111), said inner surrounding wall (114) and said bottom plate (111) cooperatively defining a mounting groove (113) therebetween;

a biosensor (2) that is mounted to said base (1) and that includes a mounting seat (21) mounted to said mounting groove (113) of said base (1), and a sensing member (22) carried by said mounting seat (21), and being adapted to be partially inserted underneath a skin surface of a host for measuring at least one analyte of the host and to send a corresponding physiological signal;

a transmitter (3) that is removably mounted to said base (1), that is for receiving and transmitting the physiological signal, and that has a bottom portion (31), said bottom portion (31) facing said base (1) when said transmitter (3) is mounted to said base (1) so as to allow said mounting seat (21) to be disposed between said base (1) and said transmitter (3) and to allow said sensing member (22) to be coupled to said transmitter (3); and a sealing unit (4) that includes a third sealing member (48) that is non-conductive and clamped between an inner peripheral surface of said inner surrounding wall (114) of said base (1) and an outer surrounding surface (213) of said mounting seat (21) for sealing a first liquid leakage pathway (a);

wherein said sealing unit (4) further includes a fourth sealing member (44) that is mounted to a top portion (214a) of a fitting hole (214) for sealing an implantation path (c).

* * * * *